United States Patent
Sadee et al.

(10) Patent No.: US 10,991,450 B2
(45) Date of Patent: *Apr. 27, 2021

(54) MATERIALS AND METHODS FOR DETERMINING METABOLIZER STATUS IN HUMANS

(71) Applicant: Ohio State Innovation Foundation, Columbus, OH (US)

(72) Inventors: Wolfgang Sadee, Upper Arlington, OH (US); Danxin Wang, Upper Arlington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 335 days.

This patent is subject to a terminal disclaimer.

(21) Appl. No.: 15/948,611

(22) Filed: Apr. 9, 2018

(65) Prior Publication Data

US 2019/0050527 A1 Feb. 14, 2019

Related U.S. Application Data

(62) Division of application No. 14/034,011, filed on Sep. 23, 2013, now Pat. No. 9,938,576.

(60) Provisional application No. 61/704,013, filed on Sep. 21, 2012.

(51) Int. Cl.
*G16B 20/00* (2019.01)
*C12Q 1/6883* (2018.01)

(52) U.S. Cl.
CPC .......... *G16B 20/00* (2019.02); *C12Q 1/6883* (2013.01); *C12Q 2600/106* (2013.01); *C12Q 2600/156* (2013.01)

(58) Field of Classification Search
CPC .............................. G16B 20/00; C12Q 1/6883
USPC .......................................................... 702/19
See application file for complete search history.

(56) References Cited

U.S. PATENT DOCUMENTS

| | | | |
|---|---|---|---|
| 5,882,944 A | 3/1999 | Sadee | |
| 6,007,986 A | 12/1999 | Sadee | |
| 6,197,505 B1 | 3/2001 | Norberg et al. | |
| 6,228,840 B1 | 5/2001 | Wei et al. | |
| 6,270,979 B1 | 8/2001 | Sadee | |
| 6,582,908 B2 | 6/2003 | Fodor et al. | |
| 6,713,488 B2 | 3/2004 | Sadee | |
| 6,812,339 B1 | 11/2004 | Venter et al. | |
| 6,953,779 B2 | 10/2005 | Wei et al. | |
| 8,071,291 B2 | 12/2011 | Bare et al. | |
| 2001/0034023 A1 | 10/2001 | Stanton et al. | |
| 2001/0049375 A1 | 12/2001 | Sadee et al. | |
| 2002/0086331 A1 | 7/2002 | Croce et al. | |
| 2003/0059774 A1 | 3/2003 | Risinger et al. | |
| 2003/0148295 A1 | 8/2003 | Wan et al. | |
| 2003/0215819 A1 | 11/2003 | Frudakis | |
| 2004/0115701 A1 | 6/2004 | Comings et al. | |
| 2004/0166519 A1 | 8/2004 | Cargill et al. | |
| 2005/0023733 A1 | 2/2005 | Burr | |
| 2005/0026169 A1 | 2/2005 | Cargill et al. | |
| 2005/0208512 A1 | 9/2005 | Sadee et al. | |
| 2005/0272054 A1 | 12/2005 | Cargill et al. | |
| 2006/0040295 A1 | 2/2006 | Kumar et al. | |
| 2006/0073479 A1 | 4/2006 | Frudakis | |
| 2007/0065821 A1 | 3/2007 | Kudaravalli et al. | |
| 2007/0197573 A1 | 8/2007 | Sadee et al. | |
| 2007/0292849 A1 | 12/2007 | Mah et al. | |
| 2008/0292584 A1 | 11/2008 | Roberts et al. | |
| 2009/0111844 A1 | 4/2009 | Sadee et al. | |
| 2010/0075308 A1 | 3/2010 | Sadee et al. | |
| 2010/0129818 A1 | 5/2010 | Sadee et al. | |
| 2010/0135463 A1 | 6/2010 | Kang et al. | |
| 2010/0167947 A1 | 7/2010 | Sadee et al. | |
| 2011/0189161 A1 | 8/2011 | Blum et al. | |
| 2011/0245492 A1 | 10/2011 | Kumar et al. | |
| 2012/0040347 A1 | 2/2012 | Sadee et al. | |
| 2014/0255930 A1 | 9/2014 | Sadee et al. | |

FOREIGN PATENT DOCUMENTS

| | | |
|---|---|---|
| JP | 2003509063 | 3/2003 |
| JP | 2005524388 | 8/2005 |
| WO | 2001020025 | 3/2001 |

(Continued)

OTHER PUBLICATIONS

Adamzik et al., "ACE I/D but no AGT (-6)A/G polymorphism is a risk factor for mortality in ARDS", European Respiratory Journal, 2007, vol. 29, pp. 482-488.

Bannon, "The Dopamine Transporter: Role in Neurotoxicity and Human Disease", Toxicology and Applied Pharmacology, 2005, vol. 204, No. 3, pp. 355-360, Abstract Only.

Brown et al., "Black Americans have an Increased Rate of Angiotensin Converting Enzyme Inhibitor-Associated Angioedema", Clinical Pharmacology and Therapeutics, 1996, vol. 60, No. 1, pp. 8-13, Abstract Only.

(Continued)

*Primary Examiner* — Jerry Lin
(74) *Attorney, Agent, or Firm* — Meunier Carlin & Curfman LLC

(57) ABSTRACT

The present invention provides methods and materials useful for determining metabolizer status. Embodiments of the present invention provide an approach using a genotyping panel and integration of genotypes of CYP3A4 and CYP3A5 to assess CYP3A metabolizer status, applicable to all CYP3A substrates, including approximately 40% of all drugs. Algorithms for CYP3A metabolizer status are described. Where the contribution ratios of CYP3A4 and CYP3A5 to overall drug levels or drug effects are known, the algorithm can be used to calculate optimal dosing. Where the contributory ratios to overall drug effects are not available, the contributory ratios can be calculated with use of the genotypes for use in drug development. Embodiments of the present invention can be used in optimizing drug treatments, selecting dose, designing therapeutics, and predicting efficacy.

9 Claims, 14 Drawing Sheets

(56) References Cited

FOREIGN PATENT DOCUMENTS

| | | |
|---|---|---|
| WO | 2004074513 | 9/2004 |
| WO | 2008136988 | 11/2008 |
| WO | 2008136989 | 11/2008 |
| WO | 2008136995 | 11/2008 |
| WO | 2008136996 | 11/2008 |
| WO | 2010111600 | 9/2010 |
| WO | 2010136790 | 12/2010 |
| WO | 2012112720 | 8/2012 |
| WO | 2013036938 | 3/2013 |

OTHER PUBLICATIONS

Chasman et al., "Genetic Loci Associated with Plasma Concentration of Low-Density Lipoprotein Cholesterol, High-Density Lipoprotein Cholesterol, Triglycerides, Apolipoprotein A1, and Apolipoprotein B Amoung 6382 White Women in Genome-Wide Analysis with Replication", Circulation: Cardiovascular Genetics, 2008, vol. 1, pp. 21-30.
DbSNP Short Genetic Variations, Reference SNP (refSNP) Cluster Report: rs35599367, Web Article accessed Jul. 15, 2014, pp. 1-2.
DbSNP Short Genetic Variations, Submitted SNP(ss) Details: ss23448194, Web Article accessed Mar. 21, 2012, pp. 1-5.
De Graan et al., "CYP3A4*22 Genotype and Systemic Exposure Affect Paclitaxel-Induced Neurotoxicity", Clinical Cancer Research, 2013, vol. 19, pp. 3316-3324.
Elens et al., "CYP3A4 intron 6 C>T SNP (CYP3A4*22) encodes lower CYP3A4 Activity in Cancer Patients, as Measured with Probes Midazolam and Erythromycin", Pharmacogenomics, 2013, vol. 14, No. 2, pp. 137-149.
Elens et al., "Effect of a New Functional CYP3A4 Polymorphism on Calcineurin Inhibitors Dose Requirements and Trough Blood Levels in Stable Renal Transplant Patients", Pharmacogenomics, 2011, pp. 1-14.
European Extended Search Report, Application No. 08754148.8 dated Apr. 16, 2010.
European Extended Search Report, Application No. 08754150.4 dated Apr. 16, 2010.
European Extended Search Report, Application No. 10756918.8 dated Sep. 27, 2012.
Exner et al., "Lesser Response to Angiotensin-Converting-Enzyme Inhibitor Therapy in Black as Compared with White Patients with Left Ventricular Dysfunction", New England Journal of Medicine (NEJM), 2001, vol. 344, No. 18, p. 1351, Abstract Only.
Feng et al., "Sequence Variation in the 3'-Untranslated Region of the Dopamine Transporter Gene and Attention-Deficit Hyperactivity Disorder (ADHD)", American Journal of Medical Genetics Part B (Neuropsychiatric Genetics), 2005, vol. 139B, pp. 1-6.
Friedel et al., "Association and Linkage of Allelic Variants of the Dopamine Transporter Gene in ADHD", Molecular Psychiatry, 2007, vol. 12, pp. 923-933.
Hegele, "SNP Judgments and Freedom of Association", Arteriosclerosis, Thrombosis, and Vascular Biology, 2002, vol. 22, pp. 1058-1061.
Hindorff et al., "Common Genetic Variation in Six Lipid-Related and Statin-Related Genes, Statin use and Risk of Incident Nonfatal Myocardial Infarction and Stroke", Pharmacogenetics and Genomics, 2008, vol. 18, pp. 677-682.
Hiroi et al., "Polymorphisms in the SOD2 and HLA-DRB1 genes are Associated with Nonfamilial Idiopathic Dilated Cardiomyopathy in Japanese", Biochemical and Biophysical Research Communications, 1999, vol. 2, pp. 332-339, Abstract Only.
Humphries et al., "Candidate Gene Genotypes, Along with Conventional Risk Factor Assessment, Improve Estimation of Coronary Heart Disease Risk in Healthy UK Men", Clinical Chemistry, 2007, vol. 53, No. 1, pp. 8-16.
Japanese Notification of Reasons for Rejection, Application No. 2012-502287 dated Aug. 13, 2014.
Johnson et al., "Polymorphisms Affecting Gene Regulation and mRNA Processing: Broad Implications ofr Pharmacogenetics", Pharmacology & Therapeutics, 2005, vol. 106, pp. 19-38.
Johnson et al., "Polymorphisms Affecting Gene Transcription and mRNA Processing in Pharmacogenetic Candidate Genes: Detection Through Allelic Expression Imbalance in Human Target Tissues", Pharmacogenetics and Genomics, 2008, vol. 18, pp. 781-791.
Johnson et al., "Promoter Polymorphisms in ACE (Angiotensin I-Converting Enzyme) Associated with Clinical Outcomes in Hyperstension", Clinical Pharmacology and Therapeutics, 2009, vol. 85, No. 1, pp. 36-44.
Johnson, "Search for Functional Alleles in the Human Genome with Focus on Cardiovascular Disease Candidate Genes", Dissertation, The Ohio State University, 2007, pp. 1-260.
Kitzmiller et al., "CYP3A4/5 Combined Genotype Analysis for Predicting Statin Dose Requirement for Optimal Liqid Control", Drug Metabolism and Drug Interactions, 2013, vol. 28, No. 1, pp. 59-63.
Lei et al., "Exonization of AluYa5 in the Human ACE Gene Requires Mutations in Both 3' and 5' Splice Sites and is Facilitated by a Conserved Splicing Enhancer", Nucleic Acids Research, 2005, vol. 33, No. 12, pp. 3897-3906, Abstract Only.
Liao et al., "The Association of CYP2C9 Gene Polymorphisms with Colorectal Carcinoma in Han Chinese", Clinica Chimica Acta, 2007, vol. 380, pp. 191-196.
Lightfoot et al., "Polymorphisms in the Oxidative Stress Genes, Superoxide Dismutase, Glutathione Peroxidase and Catalase and Risk of Non-Hodgkin's Lymphoma", Haematologica, 2006, vol. 91, pp. 1222-1227.
Ling et al., "Association Between Polymorphism of the Dopamine Transporter Gene and Early Smoking Onset: An Interaction Risk on Nicotine Dependence", Journal of Human Genetics, 2004, vol. 49, pp. 35-39.
Möllsten et al., "A Functional Polymorphism in the Manganese Superoxide Dismutase Gene and Diabetic Nephropathy", Diabetes, 2007, vol. 56, pp. 265-269.
Moyer et al., "Intronic Polymorphisms Affecting Alternative Splicing of Human Dopamine D2 Receptor Are Accociated with Cocaine Abuse", Neuropsychopharmacology, 2011, vol. 36, pp. 753-762.
Moyer, "Exploration of Functional Genetic Variants in Candidate Genes for Phsychiatric Disorders", Dissertation, The Ohio State University, 2010, pp. 1-127.
Ouellet-Morin et al., "Association of the Dopamine Transporter Gene and ADHD Symptoms in a Canadian Population-Based Sample of Same-Age Twins", American Jouranl of Medical Genetics Part B (Neuropsychiatric Genetics), 2008, vol. 147B, pp. 1442-1449.
PCT International Perliminary Report on Patentability, Application No. PCT/US2008/005539 filed Apr. 30, 2008, dated Nov. 12, 2009.
PCT International Perliminary Report on Patentability, Application No. PCT/US2010/028842 filed Mar. 26, 2010, dated Oct. 6, 2011.
PCT International Perliminary Report on Patentability, Application No. PCT/US2012/025305 filed Feb. 15, 2012, dated Mar. 20, 2014.
PCT International Perliminary Report on Patentability, Application No. PCT/US2012/054473 filed Sep. 10, 2012, dated Mar. 20, 2014.
PCT International Preliminary Report on Patentability, Application No. PCT/US2008/005540 filed Apr. 30, 2008, dated Nov. 12, 2009.
PCT International Preliminary Report on Patentability, Application No. PCT/US2008/005556 filed Apr. 30, 2008, dated Nov. 12, 2009.
PCT International Preliminary Report on Patentability, Application No. PCT/US2008/005558 filed Apr. 30, 2008, dated Nov. 3, 2009.
PCT International Search Report and the Written Opinion, Application No. PCT/US2008/005539 filed Apr. 30, 2008, dated Nov. 18, 2008.
PCT International Search Report and the Written Opinion, Application No. PCT/US2008/005540 filed Apr. 30, 2008, dated Dec. 24, 2008.
PCT International Search Report and the Written Opinion, Application No. PCT/US2008/005556 filed Apr. 30, 2008, dated Sep. 25, 2008.
PCT International Search Report and the Written Opinion, Application No. PCT/US2008/005558 filed Apr. 30, 2008, dated Nov. 5, 2008.

(56) References Cited

OTHER PUBLICATIONS

PCT International Search Report and the Written Opinion, Application No. PCT/US2010/028842 filed Mar. 26, 2010, dated Aug. 12, 2010.

PCT International Search Report and the Written Opinion, Application No. PCT/US2012/025305 filed Feb. 15, 2012, dated Jun. 8, 2012.

PCT International Search Report and the Written Opinion, Application No. PCT/US2012/054473 filed Sep. 10, 2012, dated Feb. 7, 2013.

Pinsonneault et al., "Dopamine Transporter Gene Variant Affecting Expression in Human Brain is Associated with Bipolar Disorder", Neuropsychopharmacology, 2011, vol. 36, pp. 1644-1655.

Rosatto et al., "Intron 16 Insertion of the Angiotensin Converting Enzyme Gene and Transcriptional Regulation", Nephrology, Dialysis Transplantation, 1999, vol. 14, pp. 868-871, Abstract Only.

Sadee et al., "Pharmacogenetics/Genomics and Personalized Medicine", Human Molecular Genetics, 2005, vol. 14, No. 2, pp. R207-R214.

Sayed-Tabatabaei et al. "ACE Polymorphisms", Circulation Research, 2006, vol. 98, pp. 1123-1133.

Single Nucleotide Polymorphism, Submitted SNP (ss) Details: ss12402743, Web Article accessed Jul. 23, 2008, pp. 1-3.

Solus et al., "Genetic Variation in -Eleven Phase I Drug Metabolism Genes in an Ethnically Diverse Population", Pharmacogenomics, 2004, vol. 5, No. 7, pp. 985-931.

Sotnikova et al., "Molecular Biology, Pharmacology and Functional Role of the Plasma Membrane Dopamine Transporter", CNS & Neurological Disorders-Drug Targets, 2006, vol. 5, No. 1, pp. 45-56.

Stockmann et al., "Fluticasone Propionate Pharmacogenetics: CYP3A4*22 Polymorphism and Pediatric Asthma Control", Journal of Pediatrics, 2013, vol. 162, pp. 1222-1227.

Strat et al., "The 3' Part of the Dopamine Transporter Gene DAT1/SLC6A3 is Associated with Withdrawal Seizures in Patients with Alcohol Dependence", Alcoholism: Clinical and Experimental Research, 2008, vol. 32, No. 1, pp. 27-35.

Talkowski et al., "A Network of Dopaminergic Gene Variations Implicated as Risk Factors for Schizophrenia", Human Molecular Genetics, 2008, vol. 17, No. 5, pp. 747-758.

Teft et al., "CYP3A4 and Seasonal Variation in Vitamin D Status in Addition to CYP2D6 Contribute to Therapeutic Endoxifen Level During Tamoxifen Therapy", Breast Cancer Research and Treatment, 2013, vol. 139, pp. 95-105.

Thompson et al., "Comprehensive Whole-Genome and Candidate Gene Analysis for Response to Statin Therapy in the Treating to New Targets (TNT) Cohort", Circulation: Cardiovascular Genetics, 2009, vol. 2, pp. 173-181.

Wang et al., "Intronic Polymorphism in CYP3A4 Affects Hepatic Expression and Response to Statin Drugs", Pharmacogenomics Journal, 2011, vol. 11, No. 4, pp. 274-286.

Wang et al., "Searching for Polymorphisms that Affect Gene Expression and mRNA Processing: Example ABCB1 (MDR1)", The AAPS Journal, 2006, vol. 8, No. 3, pp. E515-E520.

Wang et al., "The Making of a CYP3A Biomarker Panel for Guiding Drug Therapy", Journal of Personalized Medicine, 2012, vol. 2, pp. 175-191.

Yamada et al., "Genetic Risk for Metabolic Syndrome: Examination if Candidate Gene Polymorphisms Related to Lipid Metabolism in Japanese People", Journal of Medical Genetics, 2008, vol. 45, pp. 22-28.

Zuo et al., "ADH1A Variation Predisposes to Personality Traits and Substance Dependence", American Journal of Medical Genetics Part B: Neuropsychiatric Genetics, 2010, vol. 153B, No. 2, pp. 376-386.

| Gene | Allele | Gene location, nucleotide change | MAF | dbSNP number | Effect on CYP3A protein/activity |
|---|---|---|---|---|---|
| CYP3A4 | *1[a] | - | - | - | - |
| CYP3A4 | *22 | Intron 6, C>T | 3-6% | rs35599367 | Decreased protein |
| CYP3A4 | *6[b] | Exon 9, insA | rare | rs4646438 | Frameshift |
| CYP3A4 | *8[b] | Exon 5, G>A | rare | rs72552799 | No protein |
| CYP3A4 | *13[b] | Exon 11, C>T | rare | rs4986909 | No protein |
| CYP3A4 | *20[b] | Exon 13, insA | rare | rs7666821 | Frameshift |
| CYP3A5 | *1[a] | - | - | - | - |
| CYP3A5 | *3 | Intron3, G>A | 15-88% | rs776746 | No protein |
| CYP3A5 | *7 | Exon 11, delT | 4-21% | rs41303343 | Frameshift |

FIG. 1

| Allele 2 | Allele 2 | CYP3A4 diplotype | CYP3A4 fractional activity |
|---|---|---|---|
| *1 | *1 | *1/*1 | 1 |
| *1 | *22 | *1/*22 | 0.65 |
| *22 | *22 | *22/*22 | 0.3 |
| *1 | *6 | *1/*6 | 0.5 |
| *6 | *6 | *6/*6 | 0 |
| *1 | *8 | *1/*8 | 0.5 |
| *8 | *8 | *8/*8 | 0 |
| *1 | *13 | *1/*13 | 0.5 |
| *13 | *13 | *13/*13 | 0 |
| *1 | *20 | *1/*20 | 0.5 |
| *20 | *20 | *20/*20 | 0 |

FIG. 2A

| Allele 2 | Allele 2 | CYP3A5 diplotype | CYP3A5 fraction activity |
|---|---|---|---|
| *1 | *1 | *1/*1 | 1 |
| *1 | *3 | *1/*3 | 0.5 |
| *3 | *3 | *3/*3 | 0 |
| *1 | *7 | *1/*7 | 0.5 |
| *7 | *7 | *7/*7 | 0 |

FIG. 2B

|  | Compound | Reaction | Method |
|---|---|---|---|
| 3A4 preferred | Midazolam | 4-hydroxylation | Liver microsome |
| | Cyclosporine | | HepG2 cell expression |
| | Benzo(α)pyrene | hydroxylation | HepG2 cell expression |
| | Testosterone | 6β-hydroxylation | HepG2 cell expression |
| | Testosterone | 6β-hydroxylation | Liver microsome |
| | Testosterone | 6β-hydroxylation | Liver purified protein reconstitution |
| | Testosterone | 2β-hydroxylation | Liver purified protein reconstitution |
| | Testosterone | 15-β-hydroxylation | HepG2 cell expression |
| | Progesterone | 6β-hydroxylation | HepG2 cell expression |
| | Androstenendione | 6β-hydroxylation | HepG2 cell expression |
| | 17α-ethymylestrodiol | 2-hydroxylation | Liver microsome |
| | Aflatoxin B | 3α-hydroxylation | Bacterial expression |
| | Erythromycin | N-demethylation | Liver microsome |
| | 7-Ethoxycoumatin | O-demethylation | HepG2 cell expression |
| | Quinidine | 3-hydroxylation | Liver microsome |
| | Quinidine | N-oxidation | Liver microsome |
| | Atorvastatin | | In vivo PK, 3A5/3A4 genotype association |
| | Cyclosporine | | In vivo PK, 3A5 genotype association |

FIG. 3

| | Nifedipine | Oxdation | Bacterial expression |
|---|---|---|---|
| 3A4=3A5 | Nifedipine | oxidation | HepG2 cell expression |
| | Cortisol | 6β-hydroxylation | Liver microsome |
| | 17β-estradiol | 2-hydroxylation | Liver micorsome |
| | DHEA | 16α-hydroxylation | Liver microsome |
| | Aflatoxin B | 8,9-epoxidation | Bacterial expression |
| 3A5 preferred | *Midazolam* | *1-hydroxylation* | *Liver microsome* |
| | N-ethylmorphine | N-demethylation | Bacterial expression |
| | Erythromycin | N-demethylation | Bacterial expression |
| | d-Benzphetamine | N-demethylation | Bacterial expression |
| | Tacrolimus | | In vivo PK, 3A5 association |
| | Tacrolimus | | In vivo PK, 3A5 association |

FIG. 3 (cont.)

|  | Poor metabolizers | Intermediate metabolizers | Extensive metabolizers |
|---|---|---|---|
| Number | 19 (8%) | 167 (71%) | 49 (21%) |
| Atorvastatin dose (n=142) | 20 (10,20) | 20 (10,40) | 20 (20,40) |
| Simvastatin dose (n=84) | 20 (10,40) | 40 (20,40) | 40 (20,40) |
| Lovastatin dose (n=9) | 20 (20,20) | 20 (20,40) | --(--,--) |
| Combined dose (n=235) | 16.6 (10,20) | 23.2 (16.6,40) | 33.2 (16.6,40) |
| Age |  |  |  |
|   Combined (all three statins) | 64±12 | 63±11 | 56±9 |
| Male |  |  |  |
|   Combined (all three statins) | 13 (8%) | 113 (72%) | 32 (20%) |
| Caucasian |  |  |  |
|   Combined (all three statins) | 19 (9%) | 160 (77%) | 29 (14%) |

FIG. 4

|  |  | ≤10 mg | 20 mg | ≥40 mg |
|---|---|---|---|---|
| Poor metabolizers per dose level | Atorvastatin | 5 (45%) | 4 (36%) | 2 (18%) |
|  | Simvastatin | 2 (29%) | 3 (43%) | 2 (29%) |
| Intermediate metabolizers per dose level | Atorvastatin | 27 (27%) | 28 (28%) | 46 (46%) |
|  | Simvastatin | 4 (7%) | 18 (31%) | 36 (62%) |
| Extensive metabolizers per dose level | Atorvastatin | 5 (17%) | 11 (37%) | 14 (47%) |
|  | Simvastatin | 2 (11%) | 6 (32%) | 11 (58%) |

FIG. 5

| Gene(s) | Statistical test | Independent variables | Dependent variables | Test results |
|---|---|---|---|---|
| *Atorvastatin, simvastatin, and lovastatin (n=235)* | | | | |
| CYP3A4 | Mann-Whitney | *22 carriers vs. *22 non-carriers | Statin dose | 2-sided p=0.027 (medians 16.6 and 33.2; means 24.7 and 32.1) |
| | Ordered logistic regression | *22 carriers vs. *22 non-carriers | Statin dose level | 2-sided p=0.014; odds ratio 0.355 (95% CI=0.16-0.81) |
| CYP3A4/5 | Mann-Whitney | PMs vs. non-PMs | Statin dose | 2-sided p=0.013 (medians 16.6 and 28.2; means 22.5 and 32.2) |
| | Mann-Whitney | non-EMs vs. EMs | Statin dose | 2-sided p=0.554 (medians 20 and 33.2; means 31.2 and 32.3) |
| | Kruskal-Wallis | PMs vs. IMs vs. EMs | Statin dose | p=0.044 (medians 16.6, 23.2 and 33.2) |
| *Atorvastatin (n=142)* | | | | |
| CYP3A4 | Mann-Whitney | *22 carriers vs. *22 non-carriers | Statin dose | 2-sided p=0.199 (medians 20 and 20; means 26.9 and 33.1) |
| | Ordered logistical regression | *22 carriers vs. *22 non-carriers | Statin dose level | 2-sided p=0.129; odds ratio (95% CI=0.16,1.26) |
| CYP3A4/5 | Mann-Whitney | PMs vs. non-PMs | Statin dose | 2-sided p=0.079 (medians 20 and 20; means 22.7 and 33.4) |
| | Mann-Whitney | non-EMs vs. EMs | Statin dose | 2-sided p=0.332 (medians 20 and 20; means 31.7 and 35.7) |
| | Kruskal-Wallis | PMs vs. IMs vs. EMs | Statin dose | p=0.166 |
| *Simvastatin (n=84)* | | | | |
| CYP3A4 | Mann-Whitney | *22 carriers vs. *22 non-carriers | Statin dose | 2-sided p=0.069 (medians 20 and 40; means 27.5 and 38.4) |
| | Ordered logistical regression | *22 carriers vs. *22 non-carriers | Statin dose level | 2-sided p=0.036; odds ratio (95% CI=0.06, 0.91) |
| CYP3A4/5 | Mann-Whitney | PMs vs. non-PMs | Statin dose | 2-sided p=0.114 (medians 20 and 40; means 28.6 and 38.2) |
| | Mann-Whitney | non-EMs vs. EMs | Statin dose | 2-sided p=0.504 (medians 40 and 40; means 38.8 and 32.6) |
| | Kruskal-Wallis | PMs vs. IMs vs. EMs | Statin dose | p=0.185 |

FIG. 6

| Drug | Treatment | CYP3A4 | CYP3A5 |
|---|---|---|---|
| paclitaxel | cancer | x | |
| Auristatin | cancer | x | x |
| Everolimus | cancer | xx | |
| Flutamide | prostate cancer | xx | |
| Fulvestrant | breast cancer | xx | |
| Letrozole | breast cancer | xx | |
| Imatinib | cancer | xx | |
| Gefitinib | cancer | xx | |
| Cabazitaxel | cancer | xx | x |
| Sorafenib | cancer | xx | |
| Tamoxifen | breast cancer | x | |
| Dasatinib | CLL | xx | |
| Sunitinib malate | cancer | xx | |
| Erlotinib | cancer | xx | |
| Nilotinib | cancer | xx | |
| Docetaxel | cancer | xx | |
| Temsirolimus | cancer | xx | |
| Lapatinib | cancer | xx | |
| Alfuzosin | bening prostatic hyperplasis | xx | |
| Bortezomib | cancer | xx | |
| Pazopanib | cancer | xx | |
| Tretinoin | APL | x | x |
| Cancer related | | | |
| Fentanyl | pain | xx | |
| Palonosetron | vomiting | x | |
| Aprepitant | vomiting | xx | |
| morphine | pain | x | |
| conjugated estrogens | osteoporosis | xx | |
| Cinacalcet | hyperparathyroidism | xx | |
| Odansetron | vomiting | xx | x |
| Dexamethasone | | xx | x |
| Note: xx primary enzyme for metabolism, x enzyme involved | | | |

FIG. 7

| List of psychiatry drugs. + indicates the involvement of CYP2D6 or CYP3A4/3A5 in the metabolism of drugs ||||
|---|---|---|---|
| Name | Other name | CYP3A4/CYP3A5 | Treatment of Diseases |
| Levomilnacipran | Fetzima | + | major depressive |
| Zolpidem tartrate sublingual tablet | Intermezzo | + | insomnia |
| vilazodone hydrochloride | Viibryd | + | major depressive disorder |
| Lurasidone | Latuda | +++ | schizophrenia |
| trazodone hydrochloride | Oleptro | ++ | major depressive disorder |
| zolpidem tartrate | Edluar | + | insomnia |
| iloperidone | Fanapt | ++ | schizophrenia |
| Guanfacine extended-release | Intuniv | + | ADHD |
| valproic | Stavzor | + | bipolar manic disorder |
| aripiprazole | Abilify | ++ | schizophrenia |
| ziprasidone mesylate | Geodon | + | psychotic symptoms |
| escitalopram oxalate | Lexapro | ++ | major depressive dsorder |
| atomoxetine | strattera | + | ADHD |
| sertraline | Zoloft | + | premenstrual dysphoric mood disorder |
| fluoxetine | Prozac | + | depression |
| mirtazapine | remeron SolTab | + | depression |
| Venlafaxin | Effexor | + | anxiety disorder |
| zaleplon | Sonata | +++ | insomnia |
| citalopram | Celexa | ++ | depression |
| anafranil | clomipramine | ++ | |
| compazine | prochlorperazine | + | |
| fluvoxamine maleate | LUVOX | + | OCD |
| quetiapine | Seroquel | +++ | schizophrenia |
| donepezil | ARICEPT | + | Alzheimer's |
| risperidal | | ++ | schizophrenia |
| olanzapine | zyprexa | | psychotic disorder |
| zolpidem | intermezzo | ++ | insomnia |

FIG. 8

Relationship between genotype and metabolism phenotype for drugs with different affinity for CYP3A4 and CYP3A5. FA can be determined by activity score for a given genotype divided by the maximum activity score. FA is the fraction of enzyme activity resulting from the mutated alleles relative to the reference genotype.

| drug specificity | | 4 | 3 | ≥2 | ≥1 | <1 |
|---|---|---|---|---|---|---|
| | | 3A4*1/*1+3A5*1/*1 (FA=1) | 3A4*1/*1+3A5*3/*3 (FA$^{3A}$=0.75) | 3A4*1/*1+3A5*3/*3 (FA$^{3A}$=0.5) | 3A4*1/*22+3A5*3/*3 (FA$^{3A}$=0.30) | 3A4*22/*22+3A5*3/*3 (FA$^{3A}$=0.1) |
| 3A4=3A5 | | | 3A4*1/*1+3A5*1/*7 (FA$^{3A}$=0.75) | 3A4*1/*1+3A5*3/*7 (FA$^{3A}$=0.5) | 3A4*1/*22+3A5*3/*7 (FA$^{3A}$=0.30) | 3A4*22/*22+3A5*3/*7 (FA$^{3A}$=0.1) |
| | | | 3A4*1/*22+3A5*1/*1 (FA$^{3A}$=0.80) | 3A4*1/*1+3A5*7/*7 (FA$^{3A}$=0.5) | 3A4*1/*22+3A5*7/*7 (FA$^{3A}$=0.30) | 3A4*22/*22+3A5*7/*7 (FA$^{3A}$=0.1) |
| | | | | 3A4*1/*22+3A5*1/*3 (FA$^{3A}$=0.55) | 3A4*22/*22+3A5*1/*3 (FA$^{3A}$=0.35) | |
| | | | | 3A4*1/*22+3A5*1/*7 (FA$^{3A}$=0.55) | 3A4*22/*22+3A5*1/*7 (FA$^{3A}$=0.35) | |
| | | | | 3A4*22/*22+3A5*1/*1 (FA$^{3A}$=0.6) | | |
| | | | 3A4*1/*1+3A5*1/*1 (FA$^{3A}$=1) | 3A4*1/*1+3A5*1/*3 (FA$^{3A}$=0.90) | 3A4*1/*22+3A5*1/*3 (FA$^{3A}$=0.58) | 3A4*22/*22+3A5*1/*1 (FA$^{3A}$=0.36) |
| 3A4>3A5 | | | | 3A4*1/*1+3A5*1/*7 (FA$^{3A}$=0.90) | 3A4*1/*22+3A5*1/*7 (FA$^{3A}$=0.58) | 3A4*22/*22+3A5*3/*3 (FA$^{3A}$=0.26) |
| | | | | 3A4*1/*1+3A5*3/*3 (FA$^{3A}$=0.8) | 3A4*1/*22+3A5*3/*3 (FA$^{3A}$=0.48) | 3A4*22/*22+3A5*3/*7 (FA$^{3A}$=0.26) |
| | | | | 3A4*1/*1+3A5*3/*7 (FA$^{3A}$=0.8) | 3A4*1/*22+3A5*3/*7 (FA$^{3A}$=0.48) | 3A4*22/*22+3A5*3/*3 (FA$^{3A}$=0.16) |
| | | | | 3A4*1/*1+3A5*7/*7 (FA$^{3A}$=0.8) | 3A4*1/*22+3A5*7/*7 (FA$^{3A}$=0.48) | 3A4*22/*22+3A5*3/*7 (FA$^{3A}$=0.16) |
| | | | | 3A4*22/*22+3A5*1/*1 (FA$^{3A}$=0.68) | | 3A4*22/*22+3A5*7/*7 (FA$^{3A}$=0.16) |
| | | | 3A4*1/*1+3A5*1/*1 (FA$^{3A}$=1) | 3A4*1/*22+3A5*1/*1 (FA$^{3A}$=0.98) | 3A4*1/*1+3A5*1/*3 (FA$^{3A}$=0.592) | 3A4*1/*22+3A5*3/*3 (FA$^{3A}$=0.192) |
| | | | | 3A4*22/*22+3A5*1/*1 (FA$^{3A}$=0.84) | 3A4*1/*1+3A5*1/*7 (FA$^{3A}$=0.592) | 3A4*1/*22+3A5*3/*7 (FA$^{3A}$=0.192) |
| 3A5>3A4 | | | | 3A4*1/*1+3A5*3/*3 (FA$^{3A}$=0.6) | 3A4*1/*22+3A5*1/*3 (FA$^{3A}$=0.44) | 3A4*1/*22+3A5*7/*7 (FA$^{3A}$=0.192) |
| | | | | 3A4*1/*1+3A5*3/*7 (FA$^{3A}$=0.6) | 3A4*1/*22+3A5*1/*7 (FA$^{3A}$=0.44) | 3A4*22/*22+3A5*3/*3 (FA$^{3A}$=0.04) |
| | | | | | 3A4*22/*22+3A5*3/*3 (FA$^{3A}$=0.2) | 3A4*22/*22+3A5*3/*7 (FA$^{3A}$=0.04) |
| | | | | | 3A4*1/*1+3A5*3/*7 (FA$^{3A}$=0.2) | 3A4*22/*22+3A5*7/*7 (FA$^{3A}$=0.04) |
| | | | | | 3A4*1/*1+3A5*7/*7 (FA$^{3A}$=0.2) | |
| 3A4 only | | | | 3A4*1/*1 (FA$^{3A4}$=1) | 3A4*1/*22 (FA$^{3A4}$=0.6) | 3A4*22/*22 (FA$^{3A4}$=0.2) |
| 3A5 only | | | | 3A5*1/*1 (FA$^{3A5}$=1) | 3A5*1/*3 (FA$^{3A5}$=0.5) | 3A5*3/*3 (FA$^{3A5}$=0) |
| | | | | | 3A5*1/*7 (FA$^{3A5}$=0.5) | 3A5*3/*7 (FA$^{3A5}$=0) |
| | | | | | | 3A5*7/*7 (FA$^{3A5}$=0) |

FIG. 10

| note: | 3A4>3A5: 3A4 contribute 80%, while 3A5 20% |
| --- | --- |
| | 3A5>3A4: 3A5 contribute 80%, while 3A4 20% |
| | 3A4=3A5: 3A4 and 3A5 each contribute 50% |
| | $FA^{3A4}$: fraction activity for 3A4; $FA^{3A5}$: fraction activity for 3A5 |
| | $FA^{3A}$: combined fraction activity for 3A4 and 3A5 if drugs are metabolized by both enzymes |
| | $FA^{3A} = 1 - (CR^{EM3A4} * [1-FA^{3A4}] + CR^{EM3A5} * [1-FA^{3A5}])$ |
| | CR is contribution ratio; for example in 3A4>3A5 group, CR for 3A4 is 0.8, while CR for 3A5 is 0.2 |
| | EM3A4 or EM3A5: extensive metabolizer for 3A4 or 3A5 |

FIG. 10 (cont.)

Coding region SNPs in CYP3A4.

| Allele | variant (cDNA) | Amino acid change | Key SNP rs# | Gene location | MAF Caucasian | MAF African American | MAF Asian | MAF All (ESP) | In vitro effect | In vivo effect |
|---|---|---|---|---|---|---|---|---|---|---|
| *2 | 664 T>C | S222P | rs55785340 | Exon 7 | 0.027 | 0 | 0 | | Decreased activity | |
| *3 | 1334 T>C | M445T | rs4986910 | Exon 12 | 0-0.04 | 0-0.033 | 0 | | No change | |
| *4 | 352 A>G | I118V | rs55951658 | Exon 5 | | | 0.015-0.033 | | | Decreased activity, associated with LDL |
| *5 | 653 C>G | P218R | rs55901263 | Exon 7 | 0 | 0 | 0.006 | | | Decreased activity |
| *6 | 830_831 insA | 277 frameshift | rs4646438 | Exon 9 | | | 0.005 | | | No activity |
| *7 | 167 G>A | G56D | rs56324128 | Exon 3 | 0.014 | | | | Decreased activity | |
| *8 | 389 G>A | R130Q | rs72552799 | Exon 5 | 0.0033 | | | | No protein | |
| *9 | 508 G>A | V170I | rs72552798 | Exon 6 | 0.0024 | | | | No change | |
| *10 | 520 G>C or G>A | D174H or D174N | rs4986908 | Exon 6 | 0.003 for C | | 0.012 for A | | No change | |
| *11 | 1088 C>T | T363M | rs67784355 | Exon 11 | 0.0034 | | 0.002 | 0.001 | Decreased protein level and activity | |
| *12 | 1117 C>T | L373F | rs12721629 | Exon 11 | 0-0.004 | 0.004-0.007 | 0 | 0.001 | Decreased protein level and activity | |
| *13 | 1247 C>T | P416L | rs4986909 | Exon 11 | 0-0.004 | 0-0.021 | 0-0.021 | | No protein | |
| *14 | 44 T>C | L15P | rs12721634 | Exon 1 | | | | 0-0.003 | | |
| *15 | 485 G>A | R162Q | rs4986907 | Exon 6 | 0 | 0-0.042 | 0 | 0.014 | | |
| *16 | 554 C>G | T185S | rs12721627 | Exon 7 | | | 0.014 | 0.005 | Decreased protein level and activity | |
| *17 | 566 T>C | F189S | rs4987161 | Exon 7 | 0-0.017 | 0 | 0 | | Decreased activity | |
| *18 | 878 T>C | L293P | rs28371759 | Exon 10 | | | 0.028 | 0.01 | No change or increased activity | Low midazolam clearance, associated with bone density |
| *19 | 1399 C>T | P467S | rs4986913 | Exon 12 | 0-0.022 | 0 | 0-0.012 | | No change | Low midazolam clearance |
| *20 | 1461_1462 insA | 488 frameshift | rs7666821 | Exon 13 | <0.006 | | | | No activity | |
| *21 | 956 A>G | Y319C | | Exon 10 | | | 0.005 | | | |

FIG. 11

Mutations in CYP3A4 and CYP3A5 as potential biomarkers for predicting CYP3A activity.

| Gene | Allele | Location, variant | MAF | dbSNP number | CYP3A4 activity |
|---|---|---|---|---|---|
| CYP3A4 | *1[a] | - | - | - | - |
| CYP3A4 | *22 | Intron 6, C>T | 3%-6% | rs35599367 | Decreased protein |
| CYP3A4 | *6[b] | Exon 9, insA | rare | rs4646438 | Frameshift |
| CYP3A4 | *20[b] | Exon 13, insA | rare | rs7666821 | Frameshift |
| CYP3A5 | *1[a] | - | - | - | - |
| CYP3A5 | *3 | Intron3, G>A | 15%-88% | rs776746 | No protein |
| CYP3A5 | *7 | Exon 11, delT | 4%-21% | rs41303343 | Frameshift |

[a] Reference allele; [b] Rare variants to be considered with large-scale parallel genotyping/sequencing in clinical practice.

FIG. 12

MATERIALS AND METHODS FOR DETERMINING METABOLIZER STATUS IN HUMANS

CROSS REFERENCE TO RELATED APPLICATIONS

This application claims the priority benefit of U.S. Provisional Application No. 61/704,013, filed Sep. 21, 2012, the entire disclosure of which is expressly incorporated herein by reference for all purposes.

STATEMENT REGARDING FEDERALLY SPONSORED RESEARCH

This invention was made with government support under grant numbers R21-AI074399, K23-GM100372, U01-GM092655, and UL1-RR025755 awarded by the National Institutes of Health. The Government has certain rights in the invention.

BACKGROUND OF THE INVENTION

Genetic factors contribute to variability in the pharmacokinetics of drug metabolism. Nearly half of all drugs are metabolized by Cytochrome P450 3A4 (CYP3A4), a liver enzyme. Many drugs are designed to interact with CYP3A4, rather than other CYP enzymes thought to be polymorphic, having high inter-individual variability in function because of genetic differences. However, CYP3A4 function also varies widely among individuals.

Coding region CYP3A4 polymorphisms are rare and account for only a small portion of inter-person variability in CYP3A metabolism. Except for the promoter allele CYP3A4*1B with ambiguous effect on expression, common CYP3A4 regulatory polymorphisms were thought to be lacking. Recent studies have identified a relatively common regulatory polymorphism, designated CYP3A4*22 with robust effects on hepatic CYP3A4 expression.

CYP3A4*22 accounts for a portion of the observed variability and can be used to predict metabolizer status for drugs interacting with CYP3A4. Another CYP enzyme, namely CYP3A5, is also variably expressed in the liver. Because of the two proteins' similarity, many drugs interact with both, whereas a number of drugs are preferentially metabolized by one of either CYP3A4 or CYP3A5. Frequent deleterious mutations are known in CYP3A5, such as CYP3A5*3 and—with lower frequency—CYP3A5*7. There is a need for methods of predicting drug metabolism using CYP3A4*22 with CYP3A5 alleles *1, *3 and *7 as biomarkers for predicting overall CYP3A activity.

To predict in vivo CYP3A metabolizer status for specific drugs, a relative role of CYP3A4 versus CYP3A5 in the metabolism of each drug must be known. There is a need for tools and methods for predicting the metabolizer status of a patient and predicting the efficacy of a drug metabolized by CYP3A4 and CYP3A5 enzymatic processes.

SUMMARY OF THE INVENTION

Embodiments of the present invention provide computer-assisted methods to generate reports of the metabolizer status (fractional activity of maximum CYP3A activity) of a human for use in health/disease treatment, comprising:
a.) obtaining a nucleic acid-containing test sample from a human;
b.) conducting at least one genotyping assay of the sample so as to obtain genotype data for CYP3A4 data at rs35599367 and CYP3A5 data at rs776746 and rs41303343 in the sample, but not excluding introduction of additional rare alleles for either gene once their activity score is established;
c.) inputting the genotype data into a computer comprising an algorithm designed to analyze:
  i.) decision Table 2a and Table 2b; and
  ii.) a database of CYP3A4 and CYP3A5 metabolism impacts of at least one drug of interest;
d.) identifying the metabolizer status of the human by applying the algorithm to the genotype data; and
e.) generating a report of the metabolizer status of the human.

Also provided are computer-assisted methods to identify metabolizer status of a human for use in health/disease treatment, comprising:
a.) inputting genotyping data for CYP3A4 data at rs35599367 and CYP3A5 data at rs776746 and rs41303343 into a computer algorithm comprising the formula:

$$(AUC^{XM3A})/(AUC^{EM3A}) = 1/(1 - [CR^{EM3A4} * (1 - FA^{3A4}) + CR^{EM3A5} * (1 - FA^{3A5})]),$$

$$Dose^{XM3A} = Dose^{EM3A} * (1 - [CR^{EM3A4} * (1 - FA^{3A4}) + CR^{EM3A5} * (1 - FA^{3A5})])$$

wherein: AUC is the area under the curve; XM3A is selected from the group consisting of PM—poor metabolizer or IM—intermediate metabolizers at either CYP3A4 or 3A5, or both; EM3A4 or 3A5 is extensive metabolizer of 3A4 or 3A5; CR3A4 or 3A5 is Contribution Ratio (CR) for CYP3A4 or 3A5; FA is the fraction of the total predicted CYP3A enzyme activity relative to the reference genotype for the 3A4/5 wild-types;
b.) identifying the metabolizer status of the human by applying the algorithm to the genotype data; and
c.) generating a report of the metabolizer status of the human.

Also provided are methods to identify the metabolizer status of a human, comprising:
a.) obtaining a nucleic acid-containing test sample from a human;
b.) conducting at least one genotyping assay of the sample so as to obtain physical data regarding SNP in CYP3A4 and CYP3A5 in the sample; and
c.) identifying the human as one who has:
  i.) extensive metabolizer status if CYP3A4 genotype at rs35599367 is CC and CYP3A5 genotype at rs776746 is AA and CYP3A5 genotype at rs41303343 is a T insertion;
  ii.) intermediate metabolizer status if CYP3A4 genotype at rs35599367 is CT and CYP3A5 genotype at rs776746 is AG and CYP3A5 genotype at rs41303343 is a T deletion;
  ii.) poor metabolizer status if CYP3A4 genotype at rs35599367 is TT and CYP3A5 genotype at rs776746 is GG and CYP3A5 genotype at rs41303343 is (del T)(del T).

Also provided are such methods, wherein a human with extensive metabolizer status is further identified being at increased risk of having drug overdose or underdose or drug overdose or underdose symptoms.

Also provided are such methods, wherein a human with intermediate metabolizer status is further identified as not being at increased risk of having, drug overdose or drug overdose symptoms.

Also provided are such methods, wherein a human with poor metabolizer status is further identified being at increased risk of having drug overdose or underdose or drug overdose or underdose symptoms.

Also provided are methods of classifying a participant in a clinical trial as a poor metabolizer, intermediate metabolizer, or extensive metabolizer, with regard to CYP3A4 and CYP3A5. Embodiments further include characterizing a population of participants in a clinical trial.

Also provided are such methods, wherein the sample comprises one or more of tissue, blood, plasma, serum, urine, and feces.

Also provided are such methods, which further comprises communicating the data or risk to at least one human.

Also provided are such methods, wherein the at least one genotyping assay is selected from the group consisting of: polymerase chain reaction (PCR), DNA fragment analysis, allele specific oligonucleotide (ASO) probes, DNA sequencing, and nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA)

Also provided are such methods, which further comprises measuring the level of at least one additional liver cytochrome marker in the test sample.

Also provided are such methods, wherein said testing is performed using sequencing, 5' nuclease digestion, molecular beacon assay, oligonucleotide ligation assay, size analysis, single-stranded conformation polymorphism, or denaturing gradient gel electrophoresis (DGGE).

Also provided are such methods, wherein said nucleic acid is a nucleic acid extract from a biological sample from said human.

Also provided are such methods, in which said biological sample is blood, saliva, or buccal cells.

Also provided are such methods, wherein said assay comprises nucleic acid amplification.

Also provided are such methods, wherein said assay is performed using at least one detection reagent.

Also provided are such methods, further comprising providing a report of the identity of the SNP profile.

Also provided are such methods, further comprising providing a report of said human's increased risk for developing drug overdose or underdose symptoms.

Also provided are such methods, comprising a method of determining whether a human is in need of receiving treatment for drug overdose or underdose symptoms.

Also provided are such methods, wherein the method further comprises administering a therapeutic agent to the human.

Also provided are such methods, wherein the method further comprises decreasing the dose of a drug.

Also provided are such methods, wherein the method further comprises increasing the dose of a drug.

Also provided are such methods, further comprising preparing said nucleic acid extract from said biological sample prior to said assay.

Also provided are such methods, further comprising obtaining said biological sample from said human prior to said preparing.

Also provided are such methods, wherein said testing is performed using an allele-specific method.

Also provided are such methods, wherein said allele-specific method is allele-specific probe hybridization, allele-specific primer extension, or allele-specific amplification.

Also provided are such methods, whether a human has a decreased risk for developing drug overdose or underdose symptoms, comprising using a method herein.

Also provided are such methods, wherein the report is in paper form or computer readable medium form.

Also provided are such methods, further comprising correlating the presence of said genotype with a decreased risk for developing drug overdose or underdose symptoms.

Also provided are such methods, wherein said method comprises the use of computer software. Also provided are such methods, which are automated.

Embodiments of the invention include methods of determining coverage or denial of health insurance reimbursement and/or payment for treatments for disease based on the result of diagnostic and prognostic methods described herein. For example, a method of excluding a treatment from insurance coverage, the method comprising: identifying a patient having health insurance; receiving a result of a diagnostic procedure on the patient, wherein the diagnostic procedure comprises determining metabolizer status for the patient in relation to a drug treatment; and denying health insurance coverage for the drug treatment, if the metabolizer status is outside of a specified classification or range.

In some embodiments, a drug treatment is contraindicated if the patient is classified as a poor metabolizer, for instance, if a poor metabolizer would receive little benefit from the drug. In some embodiments, a drug treatment is contraindicated if the patient is classified as an extensive metabolizer, for instance, if an extensive metabolizer would be predicted to experience excessive or dangerous side-effects. In some embodiments, determination of metabolizer status could indicate a need for greater monitoring or cessation of a particular drug treatment.

Also provided are computer-assisted methods to determine the contribution ratio of CYP3A4 and 3A5, where unknown, to metabolism/excretion clearance of a drug suspected to be a substrate thereof, comprising:
  a.) obtaining a nucleic acid-containing test sample from a human;
  b.) conducting at least one genotyping assay of the sample so as to obtain genotype data for CYP3A4 data at rs35599367 and CYP3A5 data at rs776746 and rs41303343 in the sample, but not excluding introduction of additional rare alleles for either gene once their activity score is established;
  c.) measuring the area under the plasma/blood concentration-time curve (AUC), or measuring drug response-time course, or any other quantitative marker of drug exposure in vivo, in multiple subjects given a standard dose of the drug, and having a variety of CYP3A4/3A5 genotypes;
  d.) inputting the AUC data and genotype data into a computer comprising an algorithm as specified in 2a, designed to analyze:
    i. decision Table 2a and Table 2b; and
    ii. identifying the contribution ratio for a given drug by applying the algorithm to the genotype and AUC data; and
  e.) applying the derived contribution ratios in drug development and clinical therapeutic use to predict CYP3A metabolizer status.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE FIGURES

FIG. 1—Table 1. Polymorphisms in CYP3A4 and CYP3A5 as biomarkers for predicting CYP3A activity. [a] reference allele; [b] rare variants with clear phenotype (e.g. null alleles, or any allele with known activity score) can be readily added into the a biomarker panel when whole genome sequencing is available in clinical practice.

FIG. 2a—Table 2a. Relationship between CYP3A4 genotype and fraction activity (FA). CYP3A4*22 is assumed to have an average activity of 30% of the reference *1 allele (each *22 allele contributing 0.15 to the CYP3A4 fractional activity, and CYP3A5*3 and *7 to have 0 activity (null alleles). Any other allele of either CYP3A4 or CYP3A5 with known fractional activity, rare or newly identified, can be substituted into the algorithm to determine total CYP3A4 or 3A5 activity.

FIG. 2b—Table 2b. Relationship between CYP3A5 genotype and fraction activity (FA). As with CYP3A4, rare alleles identified by sequencing and having known effect on CYP3A5 activity can be substituted for any allele (*1, *3, *7) in a given individual. With known activity score, the metabolizer status can then be predicted from the algorithm.

FIG. 3—Table 3. Selectivity of CYP3A4 and CYP3A5 toward different compounds. The exact contributions of 3A4 and 3A5 are typically unknown, but can be determined with the algorithm presented. By measuring AUCs in multiple subjects, with varying genotypes, and using the activity scores for CYP3A4 and 3A5 alleles, CR3A4 and CR3A5 are calculated with the provided equation. In an approximation with sufficient accuracy for clinical use, an approximate relative contribution ratio (3A4/3A5) of 0.8/0.2 for CYP3A4 preferred substrates, 0.5/0.5 for 3A4=3A5; and 0.2/0.8 for CYP3A5 preferred substrates can be used.

FIG. 4—Table 4. Statin study population characteristics grouped by CYP3A4/5 combined genotype. Data for age are mean±SD. Data for number, race, and gender represent number and percentage. Data for dose represent the median (first quartile, third quartile) for each metabolizer group and statin type. Combined statin dose was calculated by first determining an atorvastatin-equivalent dose for simvastatin and lovastatin (i.e., simvastatin and lovastatin have 83% and 58% the potency, respectively, of atorvastatin).

FIG. 5—Table 5. Combined CYP3A4/5 genotype and dose levels. Data for each dose level represents the number of patients and percentage of the combined genotype group at the specified dosing level.

FIG. 6—Table 6. CYP3A4 and CYP3A4/5 analyses results. Statin dose level refers to low (<20), medium (=20), and high (>20).

FIG. 7—Table 7. CYP3A4 and/or CYP3A5 metabolize many cancer therapeutics.

FIG. 8—Table 8. CYP3A4 and/or CYP3A5 metabolize many psychiatric drugs.

FIG. 10—Relationship between genotype and metabolism phenotype for drugs with different affinity for CYP3A4 and CYP3A5. FA is defined as the ratio of the activity score for a 3A4/5 genotype over the maximum activity score for the 3A4/5 wild-types. FA is the fraction of total predicted CYP3A enzyme activity relative to the reference genotype. This table is intended to be used for drugs that are primarily metabolized by CYP3A4 and/or 3A5 (contribution of 3A4/3A5>80%). For drugs also metabolized by other enzymes, the contribution of other enzymes or excretion pathways also should be considered.

FIG. 11—Coding region SNPs in CYP3A4.

FIG. 12—Mutations in CYP3A4 and CYP3A5 as biomarkers for predicting CYP3A activity.

DETAILED DESCRIPTION OF THE INVENTION

Inter-individual variability in drug absorption, distribution, metabolism and elimination (ADME), arising from both genetic and non-genetic factors, is a main cause of therapeutic failure or undesirable adverse effects. To optimize drug response, multiple strategies have been developed to tailor individual drug therapy, employing pharmacokinetic parameters based methods, pharmacodynamic monitoring, toxicity based titration, and use of genetic biomarker tests. Genetic variants in CYP2C9, CYP2C19 and CYP2D6 are already clinically employed for predicting dosages and response for warfarin, clopidogrel, and many CYP2D6 substrate drugs. As pharmacogenomic biomarkers begin to play a prominent role in personalized medicine, predictive tests for CYP3A activity, in particular that of CYP3A4 and CYP3A5, could have substantial clinical utility.

Provided herein are methods for determining CYP3A4/CYP3A5 metabolizer status using a genotyping panel of SNPs in both of these two major drug metabolizing enzymes, including a newly identified polymorphism in CYP3A4. Combining mutations in both genes for the first time enables an assessment of CYP3A metabolizer status for a majority of drugs metabolized by these two main enzymes. The interpretation of the CYP3A4/5 genotypes is guided by an algorithm that accounts for varying affinities for each drug at CYP3A4 and CYP3A5. As most new drugs are targeted for metabolism by CYP3A4/5 rather than other CYP enzymes, this combined panel is valuable in drug development, in Phase 1-3 trials, and as a guide for optimizing an individual's drug therapy.

An important aspect resides in the integration of genotype in two genes, CYP3A4 and CYP3A5, to determine metabolizer status for drugs where the CYP3A4/CYP3A5 ratio of metabolic in vivo rates is known. Where this ratio is unknown, the CYP3A4/CYP3A5 ratios can be determined by multiple strategies, including measuring a drug's pharmacokinetics in multiple subjects and determining which genotype combination affects pharmacokinetic parameters or by adding a CYP3A4/3A5 inhibitor, such as itraconazole or ketoconazole, and measuring the changes in AUC. Determining genotype combination effects on pharmacokinetic parameters is useful in Phase II and III clinical trials, or post-FDA approval for clinical use.

In some cases, drug metabolites themselves have activity and undergo further metabolism by CYP3A, typically with unknown CYP3A4/3A5 ratios. To resolve this question, the CYP3A genotype panel can serve to establish drug responder status, such as effect and toxicity, by determining which genotype combinations yield the strongest association, and thereby enhance predictive power.

Figure 9:
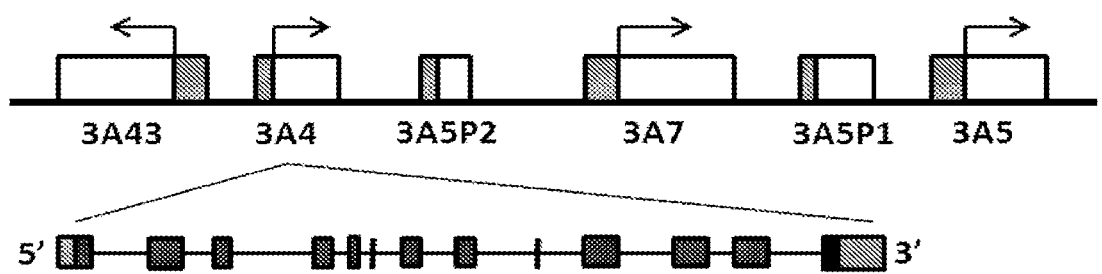
FIG. 9—Schematics of the CYP3A locus and genomic structure of CYP3A4.
Figure 13:
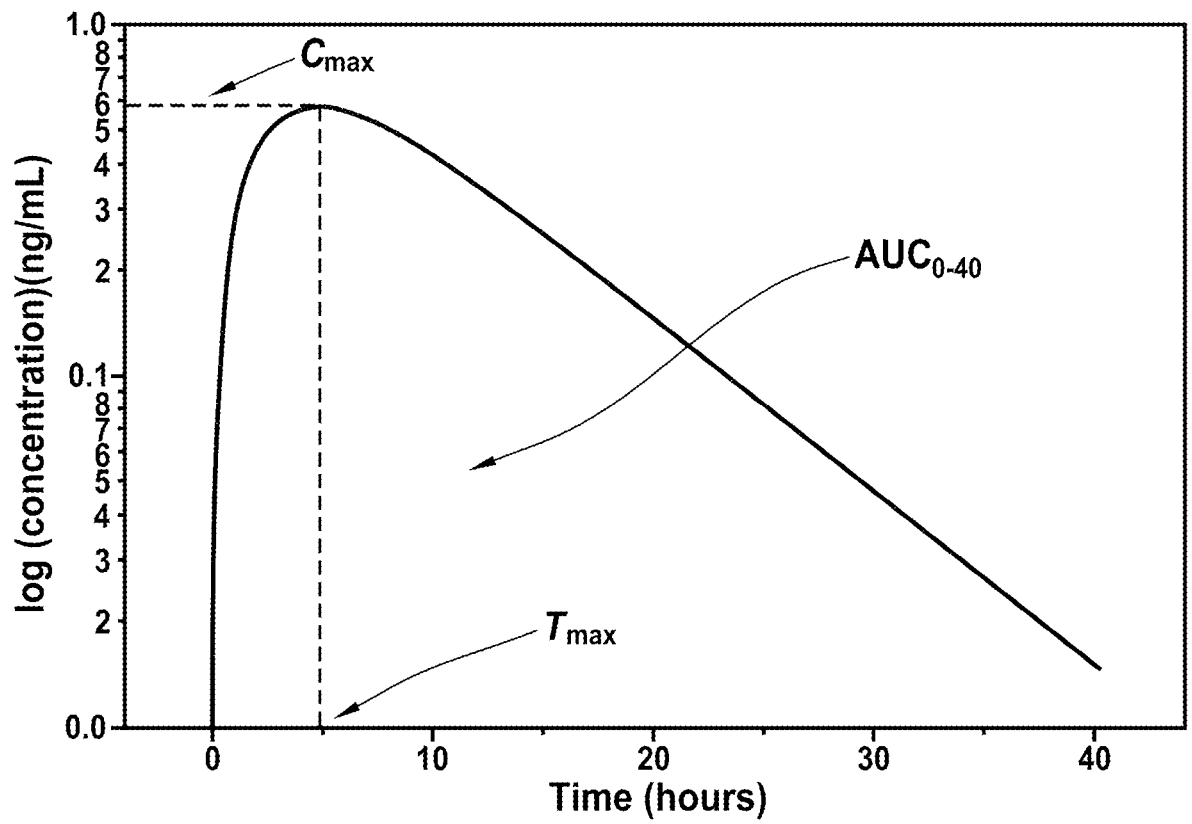
FIG. 13—Graph showing the typical profile of a drug administered as a single oral dose. Concentration of the drug is shown increasing rapidly upon administration and absorption. The concentration reaches a maximum and subsequently declines with a log-linear slope. Rapid drug metabolism would result in a steeper slope. The AUC is a measure of the systemic exposure to the drug.
Figure 14:
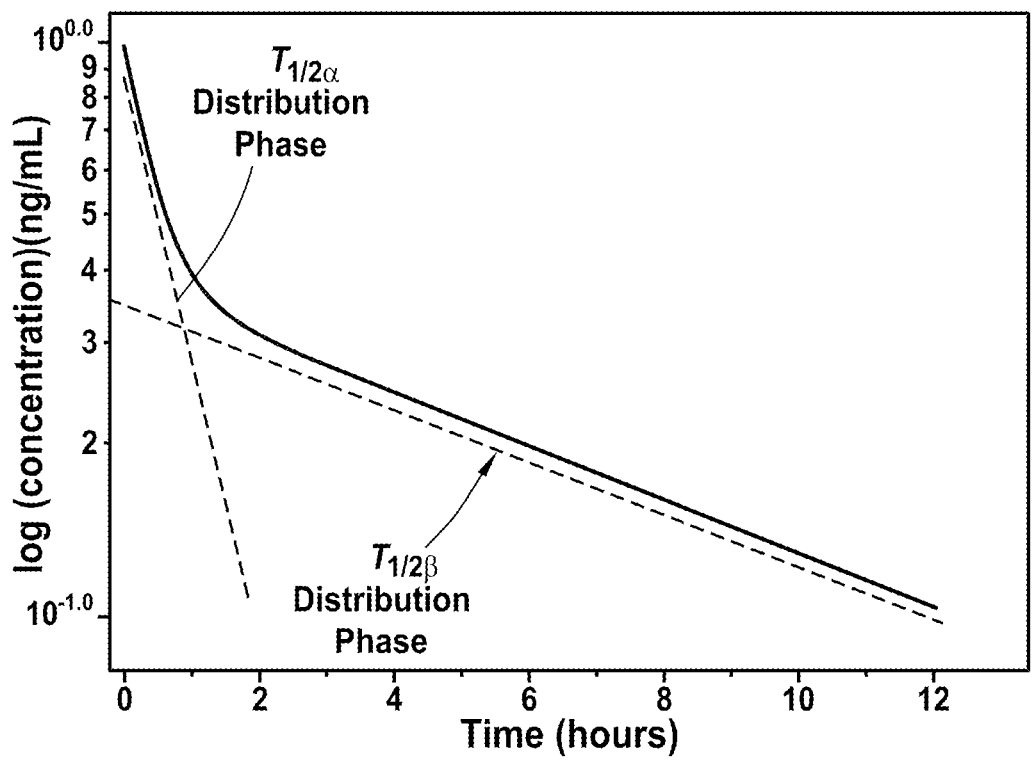
FIG. 14—Graph showing the typical profile (concentration vs. time) of a drug administered as a single bolus intravenous dose. Concentration of the drug is shown decreasing rapidly in the initial distribution phase as blood concentrations drop and the drug equilibrates with highly perfused tissues. The curve then enters the more gradual elimination phase as blood concentrations decline due to metabolism and excretion.

The four human CYP3A genes cluster on chromosome 7q21 in the order of CYP3A43, CYP3A4, CYP3A7 and CYP3A5 (FIG. 9). CYP3A4 is the most abundant isoform in liver and intestine, followed by CYP3A5 in individuals with CYP3A5*1/*1 genotype. CYP3A7 is highly and variably expressed in fetal livers, accounting for up to 50% of total cytochrome P450s, while the expression level of CYP3A7 decreases rapidly after birth and becomes undetectable in most of adult livers, except for individuals who carry two promoter variants, CYP3A7*1B and CYP3A71C. CYP3A43 is expressed at very low levels in adult livers, accounting for only 0.1-0.2% CYP3A4 transcripts. CYP3A4 and CYP3A5 have similar substrate specificity, while CYP3A7 has a smaller substrate spectrum whereas CYP3A43 does not appear to contribute substantially in drug metabolism.

Current drug design attempts to discover novel chemical entities that target CYP3A4 because it is perceived to lack strong genetic variants that affect in vivo enzyme activity, compared to other CYP enzymes such as CYP2D6. However, CYP3A4 activity nevertheless can vary up to 30-fold in the liver, which is thought to result largely from environmental factors, such as enzyme induction. Moreover, the highly similar CYP3A5 enzyme has often overlapping substrate selectivity, which can interfere with predicting in vivo drug effects.

The predictive value of genetic polymorphisms is improved with the identification of causative functional genetic variants rather than correlation markers.

Large inter-individual variability in both CYP3A4 and CYP3A5 in vivo activity has been reported numerous times in the literature. Until recently, genetic differences as a causative factor have only been described for CYP3A5, with CYP3A5*3 resulting in no detectable activity. CYP3A5*3 is highly prevalent in European Americans (EA) (allele frequency of >80%) such that a majority of subjects has no significant CYP3A5 activity, while *3 is somewhat less prevalent in African Americans (AAs) (allele frequency of ~18%) who therefore show CYP3A5 activity more frequently. AAs also carry another variant, CYP3A5*7 (allele frequency of 21%), which may also independently reduce CYP3A5 in vivo activity in subjects where *7 is not on the same allele as *3. The allele for *7 is in LD with *1 in AA and generally does not occur on the same haplotype as *3.

Recently, the inventors have described the only relatively frequent variant affecting CYP3A4 expression (CYP3A4*22, allele frequency of 5-10%); therefore, it is now possible for the first time to assess CYP3A metabolizer status using a combined genotyping assay for CYP3A4 and 3A5. Moreover, the inventors also consider several rare functional SNPs in CYP3A4 that encode no functional proteins in in vitro studies. These SNPs may become more useful when full sequencing is employed as the method of choice in clinical practice. See the Figures for additional SNPs details. Any other allele of either CYP3A4 or CYP3A5 with known fractional activity, rare or newly identified, can be substituted into the algorithm to determine total CYP3A4 or 3A5 activity.

Numerous studies have been performed to determine relative affinity of drugs for CYP3A4 versus CYP3A5, an important factor in predicting in vivo pharmacokinetics and outcomes. Owing to experimental difficulties, The CYP3A4/CYP3A5 selectivity ratios have been poorly defined for most drugs. Therefore, for many drugs it has remained controversial to what extent 3A4 and 3A5 contribute to in vivo pharmacokinetics and outcomes, the latter also reflecting the effect of active metabolites, including both drug effects and toxicity. With strong genotype effects now accessible for both CYP3A4 and CYP3A5, it is also possible to predict in vivo contribution of each CYP to drug metabolism using a genetic approach as described by Tod et al for CYP2D6 (Tod et al., *Genotype-based quantitative prediction of drug exposure for drugs metabolized by CYP2D6*, Clin. Pharmacol. Ther. 90, 582-587 (2011). The methods of Tod may be used in conjunction with the methods described herein.

The contribution of CYP3A4 or CYP3A5 to in vivo drug exposure can be assessed separately by the following equation.

$$(AUC^{XM3A})/(AUC^{EM3A})=1/(1-[CR^{EM3A4}*(1-FA^{3A4})+CR^{EM3A5}*(1-FA^{3A5})])$$

Where $AUC^{EM}$ is the AUC of the drug in patients with reference genotype (extensive metabolism phenotype, EM), while $AUC^{XM}$ is the AUC of drug in patients with mutated CYP alleles (XM refers to either poor metabolizer, PM or intermediate metabolizer, IM); CR is the contribution ratio, the fraction of a drug's apparent clearance due to metabolism by certain CYPs; FA is the fraction of enzyme activity resulting from the mutated alleles relative to the reference genotype. Individuals with EM phenotype who are homozygous for reference genotype have a FA=1, while heterozygous variant allele carriers have a FA=0.5-0.65, and homozygous variant allele carriers have a FA≤<0.32 (see FIG. 2A—Table 2a and FIG. 2B—Table 2b for relationship between genotype and fraction activity for CYP3A4 and CYP3A5, respectively). Controlling the genetic background for one CYP3A, $CR^{EM}$ for the other CYP3A can be determined by the equation shown above if AUC for individuals carrying reference alleles and AUC for individuals carrying variant alleles are known.

Alternatively, the CYP3A4/CYP3A5 affinity ratio for a drug can be assessed with use of a combined CYP3A4-CYP3A5 genotype panel (FIG. 2A and FIG. 2B). To determine this ratio, the CYP3A4-3A5 genotype panel can serve in clinical association studies, using pharmacokinetic or pharmacodynamic data, with multi-variate analyses to determine the ratios quantitatively. The resulting CYP3A4/3A5 affinity ratios then serve as a predictor for in vivo CYP3A status for any given drug, together with CR. When the contribution of CYP3A to overall drug elimination is high, as is often the case for lipophilic drugs with preferential affinity for CYP3A, the affinity ratios are the main genetic parameters to be considered in estimating CYP3A metabolizer status. Whether more accurate CYP3A4/3A5 affinity ratios over the simple classification will prove clinically useful also depends on the drug type. For some anticancer drugs, a 50% dose increase can cause severe toxicity in a patient population. If these drugs are CYP3A substrates, accurate assessment of CYP3A metabolizer status can guide the optimal dosage regimen for normal CYP3A metabolizers, with higher dose yielding more efficacy, and with lower doses applied to poor metabolizers to avoid severe toxicity.

In such a case a more accurate CYP3A4/3A5 affinity ratio could prove clinically actionable, for example CYP3A4 only, CYP3A4/CYP3A5 70/30, or 50/50, or 30/70, and CYP3A5 only. CYP3A metabolizer status, or activity score, can then be estimated from Table 2a and Table 2b (FIG. 2A and FIG. 2B).

It is anticipated that this approach will prove particularly valuable during the drug development process, as the CYP3A4/CYP3A5 affinity ratio can be determined during Phase II and III studies, with a sufficient number of subjects for multivariate analysis. Any subject lacking CYP3A5 activity and having low CYP3A4 activity is likely to experience substantially higher drug exposure than normal CYP3A metabolizers. Therefore, determining CYP3A metabolizer status may also prove essential in guiding drug therapy in clinical practice, to avoid overdosing, or to choose alternative drugs excreted by other mechanisms.

A combined use of CYP3A4/CYP3A5 genotyping has been applied to assess genetic factors in determining response to calcineurin inhibitors given to renal transplant subjects. This study contains some elements of the present disclosure but fails to provide a general guide for all drugs that are metabolized by CYP3A; specifically, this report fails to reveal the interaction between genotype status of the two enzymes CYP3A4 and 3A5, and the relative affinity for a given drug to these two enzymes, interpreted in an algorithm necessary for predicting an individual's CYP3A metabolizer status for any given drug.

Alternate Embodiment.

It is important to note that the algorithm can be used in at least two ways. Where the contribution ratios of CYP3A4 and 3A5 to overall AUC (drug levels or drug effects), the algorithm can be used to calculate optimal dosing, as described above; where the contribution ratios to overall AUC are not available, the AUCs can be measured and the contributory ratios calculated with use of the genotypes (those are the variables in the equation). This is useful for drug development, and with better definition of the relative contributory ratios, can improve predictions of proper dosing.

The algorithm relies on linear kinetics, and as such, the AUC can refer to drug plasma levels (or levels in any other body fluid/tissues) or to any drug effect or secondary marker of drug effect/toxicity. As long as any of these measures follow linear kinetics (e.g. no saturation of enzymes), which is typically the case for most CYP3A4 substrates, but not all, the method is within the scope of the present invention.

Similarly, combined CYP3A4/3A5 genotype can be used to predict dose according to the following equation:

$$Dose^{XM3A} = Dose^{EM3A} * (1-[CR^{EM3A4}*(1-FA^{3A4}) + CR^{EM3A5}*(1-FA^{3A5})])$$

Where $Dose^{EM3A}$ is the dose in patients with reference genotype, while $Dose^{XM3A}$ is the dose in patients with mutated CYP3A4 or 3A5 alleles (XM refers to either poor metabolizer or intermediate metabolizer.

EXAMPLES

Example 1. Determine the CYP3A4 Metabolizer Status

A genotyping assay was used to determine CYP3A4*22 (rs35599367 C>T), with
CC indicating extensive metabolizer status,
CT intermediate metabolizer status, and
TT poor metabolizer status.

Example 2. Determine the CYP3A5 Metabolizer Status

A genotyping assay was used to determine CYP3A5*3 (rs776746 A>G) and CYP3A5*7 (rs41303343 del T) with
*1/*1 (*3 and *7 non-carriers) indicating extensive metabolizer status,
*1/*3 or *7/*1 intermediate metabolizer status, and
*3/*3, *3/*7, or *7/*7 poor metabolizer status.

Example 3. Predict In Vivo CYP3A Metabolizer Status

Drugs were classified by the relative contributions of CYP3A4 and CYP3A5 as follows:
predominantly CYP3A4 substrate,
CYP3A4+CYP3A5 substrate, and
predominantly CYP3A5 substrate.

A more accurate CYP3A4/CYP3A5 ratio is also within the scope of the present invention, and can be established by known methodologies in vitro and in vivo. From this classification, tables are developed for each drug to predict CYP3A metabolizer status.

The prediction and classification methodology can also be utilized with known or newly discovered genetic factors influencing cytochrome P450 activity, including, for example CYP2D6.

Example 4

The CYP3A4+CYP3A5 genotyping panel is used to determine the relative contributions of CYP3A4 and CYP3A5 to pharmacodynamic or pharmacokinetic parameters.

Assessment of pharmacokinetic parameters, such as clearance and half-life, or pharmacodynamic parameters linking CYP3A status with outcomes, is a critical step in drug development. Multivariate analysis serves to establish quantitative estimates of the CYP3A4/CYP3A5 ratio. The classification may be modified as the database is modified to reflect relative contributions and yield robust in vivo predictions. For each drug, tables are established to predict CYP3A genotype status specific for that drug. It is understood that the classification/algorithm to predict the genetic contribution to CYP3A metabolizer status is but one example of how this problem can be addressed.

Example 5

The CYP3A4+CYP3A5 genotyping panel and classification table is applied in the clinic and laboratory.

The CYP3A4+CYP3A5 genotyping panel and classification table is used to adjust the drug dosage for drugs metabolized by CYP3A4/3A5, to minimize adverse effects and maximize efficacy, or guide drug discovery/development.

Example 6. CYP3A4/5 Combined Genotyping Analysis for Statin Dose Optimization

β-Hydroxy-β-methylglutaryl-coenzyme A reductase inhibitors (statins) are indicated for prevention of atherosclerotic cardiovascular disease. Metabolism of certain statins involves the cytochrome P450 3A (CYP3A) enzymes, and CYP3A4*22 significantly influences the dose needed for achieving optimal lipid control for atorvastatin, simvastatin, and lovastatin. CYP3A4/5 combined genotype approaches have proved useful in some studies involving CYP3A substrates.

In the present example, a total of 235 patients receiving stable statin doses were genotyped and grouped by CYP3A4/5 status.

The number and demographic composition of the patients categorized into the combined genotype groups were consistent with those reported for other cohorts. Dose requirement was significantly associated with the ordered combined-genotype grouping; median daily doses were nearly 40% greater for CYP3A4/5 intermediate metabolizers compared with poor metabolizers, and median daily doses were nearly double for extensive metabolizers compared with poor metabolizers.

Cardiovascular disease causes substantial morbidity and mortality. Statin therapy has proven to be highly effective in preventing the progression of cardiovascular disease for most patients, but considerable inter-individual variability in statin response and metabolism is reported. A multitude of genes and polymorphisms have demonstrated influence on statin pharmacokinetics and pharmacodynamics; however, these genetic factors by themselves are insufficient to guide therapy, and gene-gene interaction studies are largely lacking. Atorvastatin and lovastatin are primarily metabolized by cytochrome P450 3A4 (CYP3A4) and CYP3A5 in the gut and liver, and simvastatin is mainly metabolized by CYP3A4 and CYP3A5 but also by CYP2C8. The extent to which CYP3A4 and CYP3A5 contribute to statin metabolism depends on statin type and on the individual patient.

Reported findings attempting to delineate their respective contributions are not very consistent and are largely contradictory, but CYP3A4 is typically more influential. For example, CYP3A4 and CYP3A5 were determined to be responsible for 85% and 15% of atorvastatin metabolism, respectively, in a reported in vitro study. Nonetheless, inter-individual variability in CYP3A metabolism is significant (20-40-fold) and is likely to be associated with genetic variations in both CYP3A4 and CYP3A5—the two most prominent of the CYP3A enzymes.

The CYP3A4*22 single nucleotide polymorphism (SNP) has significant influence: enzyme level and activity were 1.7-2.5-fold, respectively, greater in wild type homozygous patients than in decrease of function (DOF)-allele carriers, and DOF-allele carriers required only 20%-60% of the statin dose required by homozygotic wild-type patients taking stable doses of atorvastatin, simvastatin, or lovastatin for optimal lipid control. Also, CYP3A4*22 has been associated with increased lipid-lowering response to simvastatin.

A CYP3A4/5 combined-genotype approach has utility for guiding dose selection or predicting response to certain CYP3A substrates including tacrolimus and cyclosporine. The combined genotype analysis involves categorizing individuals into one of three groups: poor metabolizers, PMs; intermediate metabolizers, IMs; or extensive metabolizers, EMs, based on their genetically-determined capacity for CYP3A4 and CYP3A5 metabolism.

Study participants were categorized into one of the following CYP3A4/5 genotype groups: PMs, IMs, or EMs. PMs were defined as individuals that were CYP3A5 non-expressers (CYP3A5*3/*3) and carriers of at least one DOF CYP3A4*22 allele, EMs were defined as individuals who were CYP3A5 expressers (CYP3A5 *1/*1 or CYP3A5 *1/*3) and CYP3A4 normal-expressers (CYP3A4 *1/*1), and IMs were defined as individuals who were CYP3A4 normal-expressers (CYP3A4 *1/*1) and CYP3A5 nonexpressers (CYP3A5 *3/*3) or who were CYP3A5 expressers (CYP3A5 *1/*1 or CYP3A5 *1/*3) and carriers of at least one DOF CYP3A4 *22 allele.

Numbers and percentages of individuals in each combined genotype group were determined and compared with those reported in the current literature. Demographic characteristics (age, gender, and race) were determined for each combined genotype group. Median, first quartile, and third quartile of atorvastatin, simvastatin, and lovastatin dose were determined for each combined genotype group. A composite statin dose (CSD) was determined after adjusting for differences in potency among the three statins. Potency differences were accounted for by normalizing the simvastatin and lovastatin doses to atorvastatin-equivalent doses (i.e., simvastatin and lovastatin have 83% and 58% the potency, respectively, of atorvastatin.

Numbers and percentages of individuals receiving statin doses within specific ranges (low, medium, and high) were determined for PMs, IMs, and EMs. $\chi^2$ analyses were utilized to determine whether the percentages of patients in each dose group were significantly different from expected frequencies.

A non-parametric one-way analysis of variance (ANOVA, Kruskal-Wallis) test was used to determine whether required statin dose was significantly different for the CYP3A4/5 combined-genotype groups (PM, IM, and EM). To compare the results with those of our previously-reported single-gene analysis approach, the CYP3A4/5 combined-genotype groups were merged so that means of only two groups (PMs vs. non-PMs and EMs vs. non-EMs) could be compared using the same type of statistical test (Mann-Whitney) used in the single-gene analysis. As ordered logistic regression cannot be applied to the multi-gene-analysis approach, results of non-parametric tests (Kruskal-Wallis) for the combined-gene approach were compared with the ordered logistic regression results of the single-gene approach. Covariates including ethnicity, gender, and age were considered in subsequent analyses to determine whether they influenced statin dose requirement in this cohort.

The numbers and percentages of individuals in each CYP3A4/5 combined-genotype group are listed in FIG. 4. The percentage of individuals in each group (8%, 71%, and 21% for PMs, IMs, and EMs, respectively) are consistent with those reported for other study populations. FIG. 4 also lists the study-population demographics (age, race, gender), and they suggest no significant associations with CYP3A4/5 combined-genotype status. The median and quartile values suggest statin dose requirement increased with the rank-ordered progression of CYP3A4/5-metabolizer status. Median daily dose requirements were 16.6, 23.2, and 33.2 mg for PMs, IMs, and EMs, respectively, in the analysis combining individuals on any of the three statins. The numbers and percentages of individuals in CYP3A4/5 combined-genotype groups for each dose level are listed in FIG. 5. For atorvastatin and simvastatin, the highest percentages of individuals in the PM group appear to occupy the lower dosing groups, and the highest percentages of individuals in the EM group appear to occupy the higher dosing groups. The $\chi^2$ analysis revealed that the proportions for IMs were significantly different from expected (0.33, 0.33, 0.33) for both atorvastatin and simvastatin, p=0.034 and p=1.7E-6, respectively. The proportions for EMs were significantly different from expected for simvastatin only, p=0.04.

The statistical results from the combined-gene analyses and the single-gene analyses are presented in FIG. 6. The p-values for the ordered logistic regression model and the Kruskal-Wallis model were 0.129 and 0.166, respectively, for atorvastatin; 0.036 and 0.185, respectively, for simvastatin; and 0.014 and 0.044, respectively, for the combined statin analysis.

Statistical significance for models that included covariates (ethnicity, gender, and age) did not differ significantly from those reported in FIG. 6; less than a 0.01 change in any p-value was observed. Additionally, including the covariates increased the Akaike information criterion and Bayesian information criterion, indicating they should not be included in the analysis of this data set.

For this cohort, CYP3A5 played a minor role in statin metabolism and the CYP3A4*22 analysis was superior for predicting statin dose requirement when compared with this example of the CYP3A4/5 combined-genotype approach. The additional consideration of CYP3A5 had limited statistical value in this analysis—in vitro studies demonstrate a minor role for CYP3A5 in statin metabolism. For CYP3A substrates relying more heavily on CYP3A5 metabolism, such as tacrolimus, the combined-genotype approach has greater analytical value.

A combined CYP3A4/5 approach is a useful tool in statin pharmacogenomic studies, especially in those involving higher proportions of non-Caucasians because non-Caucasian populations have significantly higher CYP3A5*1 allele frequencies. Although the statistical significance in this example did not improve by adding CYP3A5 into our model, CYP3A5*1 carriers did have higher dose requirements than expected based solely on their CYP3A4 status. CYP3A4 is undoubtedly the most prominent of the CYP3A enzymes, but CYP3A5 has an important role for patients with DOF CYP3A4 alleles.

A limitation of this example is that genotyping of other genes (e.g., SCL01B1, ABCB1, and CYP2C8) known to influence statin pharmacokinetics were not included in this analysis. Also, concomitant medications and statin use duration in this cohort were not well-documented; and some study results may have been obscured by not accounting for induction of CYP3A.

Example 7. CYP3A Analysis for Cancer Therapeutics

The metabolic CYP3A4/5 pathway is important in cancer therapeutics. As shown in FIG. 7, a number of cancer drugs are metabolized by one or both CYP3A4 and CYP3A5. These drugs include, but are not limited to: Resveratrol, Paclitaxel, Auristatin, Tamoxifen, Tretinoin, Palonosetron, Morphine, Everolimus, Flutamide, Fulvestrant, Letrozole, Imatinib, Gefitinib, Cabazitaxel, Sorafenib, Dasatinib, Sunitinib malate, Erlotinib, Nilotinib, Docetaxel, Temodar, Temsirolimus, Lapatinib, Alfuzosin, Bortezomib, Pazopanib, Fentanyl, Aprepitant, conjugated estrogens, Cinacalcet, Odansetron, and Dexamethasone.

Example 8. CYP3A Analysis for Psychiatric and CNS Drugs

As shown in FIG. 8, a number of psychiatric drugs are metabolized by one or both CYP3A4 and CYP3A5. These drugs include, but are not limited to: levomilnacipran, vilazodone hydrochloride, zolpidem tartrate, guanfacine extended-release, valproic, ziprasidone mesylate, atomoxetine, sertraline, fluoxetine, mirtazapine, venlafaxin, compazine, prochlorperazine, fluvoxamine maleate, donepezil, trazodone hydrochloride, iloperidone, aripiprazole, escitalopram oxalate, citalopram, anafranil, clomipramine, risperidal, zolpidem, Lurasidone, zaleplon, and quetiapine.

Example 9. Genetic Variation and Interaction Between CYP3A4 and CYP3A5

Because drugs metabolized by CYP3A4 are often also CYP3A5 substrates, while CYP3A5 expression is comparable to that of CYP3A4 in some individuals, CYP3A5 contributes substantially to inter-individual variability in CYP3A activity. Therefore, the interaction between CYP3A4 and CYP3A5 polymorphisms is important. The most frequent polymorphism in CYP3A5 (*3, rs776746), causing aberrant splicing and abolishing CYP3A5 mRNA and enzyme activity (FIG. 12), is highly prevalent in Caucasians (>80%) but less frequent in African Americans (<20%). Since CYP3A4*22 and CYP3A5*3 are in very low LD, loss of CYP3A function caused by *22 can be compensated by CYP3A5 expression in individuals carrying the wild-type CYP3A5*1 allele. CYP3A5*3 has been associated with tacrolimus/cyclosporine pharmacokinetics. Because tacrolimus is preferentially metabolized by CYP3A5, and cyclosporine by CYP3A4, it is contemplated that observed inconsistent associations are due to neglecting the activity and functional polymorphism in CYP3A4. With discovery of the relatively common functional polymorphisms *22 in CYP3A4, it is now possible to test the in vivo effects of the combination of CYP3A4 and CYP3A5 alleles on CYP3A activity. For example, the association between *22 and simvastatin-mediated cholesterol reduction is stronger when analyzed only in individuals who carry CYP3A5*3/*3 than in the entire cohort. Similarly, the association between *22 and tacrolimus pharmacokinetics and tacrolimus/cyclosporine dose requirements became stronger when CYP3A5 *3 genotype is considered. Moreover, it is contemplated that CYP3A7 variants CYP3A7*1B and CYP3A7*1C contribute to inter-person variability in CYP3A activity for some substrates—especially steroids in adult livers.

Example 10. Polymorphisms in Transcription Factors

CYP3A4 is subject to regulation by several transcription factors, including liver enriched transcription factors and nuclear receptor family. The expression of CYP3A4 mRNA is correlated with the expression of PXR, CAR, HNF4a, FOXA2, and others. Therefore, polymorphisms present in these transcription factors could regulate the constitutive and inducible expression of CYP3A4. However, coding region SNPs in PXR and CAR are rare. Common polymorphisms in promoter, intron, or downstream regions have been identified in PXR, some significantly associated with CYP3A4 mRNA expression or enzyme activity. rs2472677 has been associated with unboosted atazanavir clearance, while a PXR haplotype was associated with CYP3A4 and ABCB1 mRNA expression and doxorubicin clearance in Asian breast cancer patients. Associations between PXR, CAR and HNF4a genotype and docetaxel/doxorubicin pharmacokinetics show that polymorphisms in transcription factors have the potential to affect CYP3A4 expression, but account only for a portion of inter-individual variability in CYP3A4 expression and enzyme activity, being confounded by environmental conditions that impact multiple transcription factor expression. In addition, PXR, CAR and other transcriptions factors are subject to alternative splicing, with splice variants having different activities in DNA binding or ligand binding.

Example 11: microRNA and Epigenetics Regulation

CYP3A4 expression is further regulated directly or indirectly by miRNAs. miR-27b binds to a CYP3A4 3'UTR target sequence and decreases CYP3A4 mRNA and protein expression, thereby reducing in vitro sensitivity of PANC1 cells to cyclophosphamide. Moreover, CYP3A4 expression can be regulated indirectly by miR-148a or miR-27b via targeting PXR or VDR. Furthermore, CYP3A4 expression may be regulated by epigenetic modifications directly or indirectly through transcription factor PXR. Regulatory events contribute to the large inter-individual variability of hepatic CYP3A4. Biomarker panels including the evaluation of miRNA expression in conjunction with genotype are contemplated.

Example 10. Genetic Variation in CYP3A4/5 in Population Subgroups

Allelic frequency varies by subpopulation and racial groups. This variation influences CYP3A4/5 metabolizer status. Ideal genetic markers are functional, causative variants rather than correlation markers. Functional variants are predictive, regardless of race, though they may occur with predictable frequency in particular racial populations. Polymorphisms identified by associations often lack a clear mechanistic role and often represent only tagging SNPs, masking the effect size of true regulatory variants.

Studies have focused on promoter SNP rs2740574 (CYP3A4 *1B, −392 A>G, MAF 5.4% in Caucasians and 35% in non-Caucasians). CYP3A4*1B is in LD with the fully active CYP3A5*1 reference allele in African Americans, indicating that CYP3A5 activity could account for clinical phenotype associated with CYP3A4 *1B.

Additional regulatory variants reside in intron 7 (SNP rs4646437), intron 10 SNP (rs2242480), and in enhancer regions. Intron 7 SNP rs4646437 is associated with CYP3A4 protein expression and enzyme activity in human liver microsomes. The intron 10 SNP CYP3A4*1G (rs2242480) is associated with lipid-lowering efficacy of atorvastatin, tacrolimus pharmacokinetics in renal transplant patients, risk of coronary heart disease, and severity of withdrawal symptoms in methadone maintenance patients, all studies performed in Asian populations. The effect of CYP3A4 *1G on mRNA/protein level is interesting. In reporter gene assays, the minor G allele resulted in reduced transcription, indicating a loss of function. The G allele was associated with lower dose-adjusted blood levels (AUC) of tacrolimus in vivo. CYP3A4 *1G is in high LD with CYP3A5 *1 in Japanese individuals. Variants in the enhancer region of CYP3A4 include rs2737418 (−7206 upstream), associated with CYP3A4 enzyme activity in livers from African Americans. The minor T allele has been associated with higher enzyme activity but lower mRNA levels. Reporter gene assays suggest an effect for a TGT insertion (rs34401238, −11 kb upstream) on CYP3A4 transcription. Some inconsistent clinical associations previously observed with CYP3A4 variants may be caused, in part, by LD with CYP3A5*1.

An intron 6 SNP (rs35599367, designated as *22) in CYP3A4 strongly affects hepatic expression and is associated with statin dose requirements. Measuring allelic CYP3A4 heteronuclear RNA (hnRNA) and mRNA expression in human livers using multiple marker SNPs, marked allelic expression imbalance was found in 13% of samples. Genotyping and sequencing the CYP3A4 locus identified intron 6 SNP rs35599367, which fully accounted for the allelic CYP3A4 expression imbalance; with the minor T allele expressed 1.6-5 fold less than the main C allele. Consistently, CYP3A4 mRNA and enzyme activity in livers with CC genotype were higher than CT and TT carriers. Without wishing to be bound by theory, in vitro minigene transfection assays suggest that the T allele affects nascent RNA elongation. Consistent with reduced enzyme activity supported by CYP3A4*22, *22 is associated with tacrolimus pharmacokinetics in kidney transplant recipients, cyclosporine and tacrolimus trough blood levels and dose requirements, simvastatin-mediated cholesterol reduction, and increased risk of delayed graft function and worse renal function in cyclosporine-treated kidney transplant patients. The allele frequency of *22 is 3-6% in Caucasian population and may be lower in subjects of African descent. Because CYP3A4 metabolizes nearly 50% of clinically used drugs, *22 is a useful biomarker to predict drug dosage, efficacy, and adverse effects. As CYP3A4 *22 is embedded in main reference haplotype, lacking substantial LD with any other HapMap SNPs, its presence and relevance had earlier escaped detection in genome-wide association studies built on tagging SNP panels.

Example 11: Coding Region Polymorphisms

More than 20 non-synonymous coding region SNPs have been reported for CYP3A4 with low minor allele frequency (MAF) for each (FIG. 11). A critical analysis of these variants is essential for biomarker panel development.

CYP3A4 *2, *3, *7, *9, *10, *16, *17 and *19 support similar protein expression compared to the reference allele *1, measured in a bacterial expression system. CYP3A4*3, *7, *9, *10 and *19 also did not change enzyme activity, while CYP3A4 *2, *7, *16 and *17 caused substrate specific changes in enzyme activity. CYP3A4*3 was associated with lower levels of low-density lipoprotein cholesterol in hypercholesterolemia patients and with a higher HDL increase upon fluvastatin treatment. CYP3A4*3 was not associated with changes in LDL level after atorvastatin treatment, a CYP3A4 substrate, weighing against a substantial effect on enzyme activity and hence drug effect. In Japanese cancer patients receiving paclitaxel, *1/*16 carriers showed a 20% lower median AUC ratio of 3'-p-hydroxypaclitaxel to paclitaxel and a 2.4 fold higher median AUC ratio of 6α-hydroxypaclitaxel to paclitaxel, compared to *1/*1 carriers, indicating *16 is associated with reduced 3'-p-hydroxylation of paclitaxel.

CYP3A4 *8 and *13 did not yield detectable P450 holoproteins in a bacterial expression system, indicating they may affect protein translation or stability. Similarly, CYP3A4 *11 and *12 showed less protein expression than *1 in in vitro expression system, while CYP3A4*12 also altered substrate-specific enzyme activity. *8 and *13 occur in the population at very low allele frequencies.

CYP3A4 *4, *5 and *6 occur only in Asian populations with MAF of 1.5-3%, <1%, and <1%, respectively. Subjects heterozygous for *4, *5, and *6 displayed decreased urinary ratios of 6β-hydroxycortisol over cortisol as a measure of CYP3A4 activity, in subjects taking additional drugs such as ketoconazole. After 4 weeks of oral administration of 20 mg simvastatin, *4 carriers had greater reduction in triglycerides and total cholesterol than non-carriers. As CYP3A4 *6 represents an A insertion causing a frameshift, it is inferred to abolish CYP3A4 enzyme activity.

CYP3A4*15 exists only in African Americans with MAF of 4.2%. One study found that individuals with *15 also express CYP3A5, indicating *15 may be in LD with CYP3A5 *1. On the other hand, CYP3A4*18 is specific to Asian population with MAF of 2.8%. In vitro expression results indicate that *18 expresses similar protein levels as *1 and did not alter catalytic activity. Yet, in 13 subjects heterozygous for *18 and 26 control subjects, *18 carriers showed diminished midazolam clearance compared to non-carriers (and also with low lumbar spine bone mass density), indicating *18 is associated with decreased catalytic activity for midazolam. Molecular modeling suggested structural change in substrate recognition sites in *18 compared to *1. In contrast, *18 was associated with decreased $C_{max}$ and AUC, and increased clearance of cyclosporine in healthy Chinese subjects, suggesting higher enzymatic activity. Similarly, *18 was associated with increase clearance i8 of tacrolimus in healthy Chinese subjects, and in renal transplant recipients. Yet, in Japanese cancer patients, *18 was not associated with paclitaxel pharmacokinetic parameters. These results are compatible with the hypothesis that *18 has substrate-specific properties. In a cohort of 2125 Korean women, *18 was in high linkage disequilibrium (LD) with CYP3A5*3 (D'=0.8). As discussed earlier, high LD between haplotypes spanning CYP3A4 and CYP3A5 confounds conclusion about CYP3A4 activity by effects on CYP3A5.

CYP3A4*20 has a MAF of <0.6% in Caucasian population. Representing an A insertion, *20 shifts the open reading frame and creates a premature stop codon yielding a truncated protein. In yeast and HEK cell expression system, *20 showed low protein expression lacking catalytic activity for midazolam. One subject heterozygous for *20 showed reduced systemic midazolam clearance. The evidence for *20 abolishing CYP3A4 activity is strong.

The MAF's of coding region SNPs are exceedingly low. Non-synonymous SNPs with MAF>1% either did not change activity/protein expression or their functions have not been fully characterized (*2, *3, *7, *9, *10, *15, *17, *19). CYP3A4 *4, *5, *6, *8, *11, *12, *13, *16 and *20 are indicated to decrease protein expression and/or enzyme activity, but display MAF's<1%, mostly in only one ethnic group, and with varying degree of evidence supported a robust effect on CYP3A4 activity. Anticipating the arrival of large scale sequencing in clinical practice, it now becomes imperative to assess the impact of variants with low minor allele frequency, as these will become available when full sequences are being deployed. Some rare coding region variants (for example, SNPs that shift open reading frame or encode an unstable protein like *6, *20, *8, *11, *12 and *13) are projected to have significant impact on drug metabolism in individuals who carry them and provide valuable biomarkers for predicting CYP3A activity in comprehensive biomarker panels. In FIG. 12, alleles associated with functional variation are presented.

Example 12. Clinical Applications

Although coding region polymorphisms of CYP3A4 are included in the Affymetrix drug-metabolizing enzymes and transporters panel (DMET plus), they usually are not detected because of MAF<1% in Caucasian or Caucasian/African American mixed populations. Therefore, their impact on clinical phenotypes can be assessed only by inference from in vitro studies, unless very large cohorts are studied—limiting their clinical utility. CYP3A4*18 is relatively frequent in Asian population, showing some clinical associations. Because CYP3A4*18 is in LD with CYP3A5*1, the independent effect of CYP3A4*18 may be limited. CYP3A5 *3 is a biomarker with moderate utility for predicting tacrolimus dose in combination with clinical factors, and could be more useful if also assessing CYP3A4 polymorphisms. The regulatory CYP3A4*22 allele (rs35599367) is a useful biomarker for predicting CYP3A4 enzyme activity. Combined with CYP3A5 genotype (*1, *3 and *7), it is now possible to categorize individuals into poor, intermediate and extensive metabolizer phenotypes for overall CYP3A activity. Indeed, a combination of CYP3A4 and CYP3A5 genotypes predicted tacrolimus/cyclosporine dose or pharmacokinetics parameters better than CYP3A4 or CYP3A5 genotype alone.

Multiple factors regulate CYP3A4 expression/enzyme activity. The relatively common regulatory polymorphism, rs35599367 (CYP3A4*22), has characteristics of a good biomarker. While the *22 allele contributes a relatively small portion to overall population variance in CYP3A4 activity, owing to its relatively low allele frequency, it does have significant influence on those subjects carrying the minor allele. Homozygous carriers of *22 may be rare (<<1%), but given the large number of subjects taking CYP3A4 substrate drugs, such individuals may experience unusual drug effects. Combined with other variants in CYP3A5 (such as *3 and *7), it is now possible to predict a larger portion of the genetic components contributing to overall CYP3A enzyme activity toward CYP3A substrate drugs across different racial groups. Additional mutations with effect on enzyme activity can be further incorporated into the predictive panel as clinical genotyping/sequencing is routinely performed on a broader scale.

Additional genetic variation is relevant to drug metabolism and can be used in the methods described.

Examples of variation relevant to drug metabolism for CYP3A4 include: rs12333983 (T>A), rs12721627 (G>C), rs12721634 (A>G), rs1851426 (A>G), rs2242480 (C>T), rs2246709 (A>G), rs2687116 (C>A), rs2740574 (C>T), rs28371759 (A>G), rs3735451 (T>C), rs4646437 (G>A), rs4646440 (G>A), rs4986910 (A>G), rs4986913 (G>A), rs4986914 (A>G), rs4987161 (A>G), and rs6956344 (C>T).

Examples of variation relevant to drug metabolism for CYP3A5 include: rs10264272 (C>T), rs15524 (A>G), rs17161788 (T>C), rs41303343 (->A), rs4646457 (A>C), and rs4646458 (T>G).

Specific examples are provided, describing how the algorithm can be used for selecting drugs used in the therapy of cardiovascular disorders, CNS disorders, cancer, and immune reactions. It is understood that CYP3A4 and CYP3A5 are involved in the metabolism of numerous drugs, and that these are only representative examples. Correct dosing of the selected drugs can have important clinical consequences, for example: preventing long-term overdosing of statins—possibly leading to cognitive problems and rhabdomyolysis; reducing adverse effects and enhancing efficacy of immunosuppressant drugs, particularly organ transplant rejection or drug toxicity due to overdosing, a condition which lacks valid predictive biomarkers; and anticancer drugs—allowing higher and more effective dosing in extensive metabolizers while maintaining current dosing recommendations for reduced metabolizers developed based on drug toxicity frequency across the entire population; and CNS active drugs—selecting choice of drug in poor CYP3A4/5 metabolizers, attaining optimal dosing, preventing non-response and toxicity.

Adjustment in the application of the algorithm in the selectivity of drugs can be made to improve its application following larger clinical trials when the provided algorithm can be used to attribute relative contributions of CYP3A4 and CYP3A5 to phenotype variability in characteristics such as dosage, efficacy, and toxicity.

Cardiovascular diseases may be treated by statins, lipid lowering drugs, such as atorvastatin, lovastatin, and simvastatin. They are currently thought to be mainly metabolized by CYP3A4. Therefore, dose adjustment would be:

Genotype 3A4*1/3A4*22 (FA=0.6),adjusted dose=$Dose^{EM3A}*0.6=0.6*Dose^{EM3A}$

Genotype 3A4*22/3A4*22 (FA=0.2),adjusted dose=$Dose^{EM3A}*0.2=0.2*Dose^{EM3A}$

Organ transplant recipients are frequently treated with immunosuppressive drugs, tacrolimus and cyclosporine. Tacrolimus is 3A5>3A4, while cyclosporine is 3A4>3A5. Therefore dose adjustment would be:

For tacrolimus:

Genotype 3A4*1/3A4*22+3A5*3/3A5*3(FA=0.192), adjusted dose=$Dose^{EM3A}*0.192=0.192*Dose^{EM3A}$ Genotype 3A4*22/3A4*22+3A5*3/3A5*1(FA=0.44), adjusted dose=$Dose^{EM3A}*0.44=0.44*Dose^{EM3A}$ Genotype 3A4*1/3A4*1+3A5*1/3A5*3(FA=0.6), adjusted dose=$Dose^{EM3A}*0.6=0.6*Dose^{EM3A}$ For cyclosporine:

Genotype 3A4*1/3A4*22+3A5*3/3A5*3(FA=0.48), adjusted dose=$Dose^{EM3A}*0.48=0.48*Dose^{EM3A}$ Genotype 3A4*22/3A4*22+3A5*3/3A5*3(FA=01.6), adjusted dose=$Dose^{EM3A}*0.16=0.16*Dose^{EM3A}$ Genotype 3A4*1/3A4*1+3A5*1/3A5*3(FA>0.9), adjusted dose=$Dose^{EM3A}*0.9=0.9*Dose^{EM3A}$ Anticancer drugs include, for example, tyrosine kinase inhibitors such as imatinib, gefitinib, sorafenib, sunitinib, and the mTOR inhibitor temsirolimus which are all metabolized by CYP3A enzymes. The relative weight or which CYP3A enzyme is the predominant one is not known with certainty for some of these drugs. So an approximation may be made, by assuming they are metabolized equally by both 3A4 and 3A5, 3A4=3A5. Therefore dose adjustment for CYP3A4/5 substrates would be:

Genotype 3A4*1/3A4*22+3A5*1/3A5*1(FA=0.8), adjusted dose=$Dose^{EM3A}*0.8=0.8*Dose^{EM3A}$ Genotype 3A4*22/3A4*22+3A5*1/3A5*1(FA=0.6), adjusted dose=$Dose^{EM3A}*0.6=0.6*Dose^{EM3A}$ Genotype 3A4*1/3A4*22+3A5*3/3A5*3(FA=0.3), adjusted dose=$Dose^{EM3A}*0.3=0.3*Dose^{EM3A}$ Alternately, as CYP3A4 is frequently the primary CYP3A enzyme for many drugs, an approximation could be made to assume 3A4>3A5 when relative weight is not known with certainty. A list of anticancer drugs that are substrates for CYP3A4 and/or CYP3A5 is provided in FIG. 7.

Central nervous system (CNS) diseases are also treated by drugs metabolized by CYP3A enzymes. For example, schizophrenia drugs lurasidone and quetiapine are metabolized by CYP3A enzymes, but it is unknown whether they are metabolized by only one or both. An approximation may be made, by assuming they are metabolized equally by 3A4 and 3A5, thus, the dose adjustment would be same as with the anticancer drugs shown above. A table with CYP3A4/5 CNS drugs is provided in FIG. 8.

Thus, the general formula can be applied in clinical prediction of dose by genotype. The general dose formula is: $Dose^{XM3A}=Dose^{EM3A}*(1-[CR^{EM3A4}*(1-FA^{3A4})+CR^{EM3A5}*(1-FA^{3A5})])$ or $Dose^{XM3A}=Dose^{EM3A}*FA^{3A}$. $FA^{3A}$ can be calculated from 3A activity score based on individuals' 3A4/3A5 genotypes and whether the drug is metabolized by 3A4, 3A5 alone or both. The formula is: $FA^{3A}=1-[CR^{EM3A4}*(1-FA^{3A4})+CR^{EM3A5}*(1-FA^{3A5})]$. FIG. 10 shows fractional activity (FA) values for genotype combinations.

DEFINITIONS AND METHODS

Single Nucleotide Polymorphisms (SNPs)

Those skilled in the art will readily recognize that nucleic acid molecules may be double-stranded molecules and that reference to a particular site on one strand refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Probes and primers may be designed to hybridize to either strand and SNP genotyping methods disclosed herein may generally target either strand. Throughout the specification, in identifying a SNP position, reference is generally made to the protein-encoding strand, only for the purpose of convenience.

References to variant peptides, polypeptides, or proteins of the present invention include peptides, polypeptides, proteins, or fragments thereof, that contain at least one amino acid residue that differs from the corresponding amino acid sequence of the art-known peptide/polypeptide/protein (the art-known protein may be interchangeably referred to as the "wild-type," "reference," or "normal" protein). Such variant peptides/polypeptides/proteins can result from a codon change caused by a nonsynonymous nucleotide substitution at a protein-coding SNP position (i.e., a missense mutation) disclosed by the present invention. Variant peptides/polypeptides/proteins can also result from a nonsense mutation, i.e., a SNP that creates a premature stop codon, a SNP that generates a read-through mutation by abolishing a stop codon, or due to any SNP disclosed herein that otherwise alters the structure, function/activity, or expression of a protein, such as a SNP in a regulatory region (e.g. a promoter or enhancer) or a SNP that leads to alternative or defective splicing, such as a SNP in an intron or a SNP at an exon/intron boundary. As used herein, the terms "polypeptide," "peptide," and "protein" are used interchangeably.

Nucleic Acid Molecules and SNP Detection Reagents & Kits

The Tables herein provide a variety of information about CYP3A SNPs associated with drug metabolism. Provided are isolated nucleic acid molecules that contain one or more SNPs, as disclosed in the Tables. Isolated nucleic acid molecules containing one or more SNPs disclosed in at least one of the Tables herein may be interchangeably referred to throughout the present text as "SNP-containing nucleic acid molecules." Isolated nucleic acid molecules may optionally encode a full-length variant protein or fragment thereof. The isolated nucleic acid molecules also include probes and primers, described in greater detail in the section entitled "SNP Detection Reagents," which may be used for assaying the disclosed SNPs, and isolated full-length genes, transcripts, cDNA molecules, and fragments thereof, which may be used for such purposes as expressing an encoded protein.

As used herein, an "isolated nucleic acid molecule" generally is one that contains a SNP of the present invention or one that hybridizes to such molecule such as a nucleic acid with a complementary sequence, and is separated from most other nucleic acids present in the natural source of the nucleic acid molecule. Moreover, an "isolated" nucleic acid molecule, such as a cDNA molecule containing a SNP, can be substantially free of other cellular material, or culture medium when produced by recombinant techniques, or chemical precursors or other chemicals when chemically synthesized. A nucleic acid molecule can be fused to other coding or regulatory sequences and still be considered "isolated." Further examples of DNA molecules include recombinant DNA molecules maintained in heterologous host cells, and purified (partially or substantially) DNA molecules in solution. RNA molecules include in vivo or in vitro RNA transcripts of the isolated SNP-containing DNA molecules. Nucleic acid molecules further include such molecules produced synthetically.

Generally, a SNP-containing nucleic acid molecule comprises one or more SNP positions with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon), especially if the SNP-containing nucleic acid molecule is to be used to produce a protein or protein fragment.

For full-length genes and entire protein-coding sequences, a SNP flanking sequence can be, for example, up to about 5 KB, 4 KB, 3 KB, 2 KB, 1 KB on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Furthermore, fragments of such full-length genes and transcripts that contain one or more SNPs disclosed herein are also encompassed by the present invention, and such fragments may be used, for example, to express any part of a protein, such as a particular functional domain or an antigenic epitope.

Thus, the present invention also encompasses fragments of the nucleic acid sequences as disclosed herein and their complements. A fragment typically comprises a contiguous nucleotide sequence at least about 8 or more nucleotides, or at least about 12 or more nucleotides, or at least about 16 or more nucleotides. Further, a fragment could comprise at least about 18, 20, 22, 25, 30, 40, 50, 60, 80, 100, 150, 200, 250 or 500 (or any other number in-between) nucleotides in length. The length of the fragment will be based on its intended use. For example, the fragment can encode epitope-bearing regions of a variant peptide or regions of a variant peptide that differ from the normal/wild-type protein, or can be useful as a polynucleotide probe or primer.

Such fragments can be isolated using the nucleotide sequences provided herein for the synthesis of a polynucleotide probe. A labeled probe can then be used, for example, to screen a cDNA library, genomic DNA library, or mRNA to isolate nucleic acid corresponding to the coding region. Further, primers can be used in amplification reactions, such as for purposes of assaying one or more SNPs sites or for cloning specific regions of a gene.

An isolated nucleic acid molecule further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a SNP disclosed herein. Such primers may be used to amplify DNA of any length so long that it contains the SNP of interest in its sequence.

As used herein, an "amplified polynucleotide" of the invention is a SNP-containing nucleic acid molecule whose amount has been increased at least two fold by any nucleic acid amplification method performed in vitro as compared to its starting amount in a test sample. In other embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used.

Generally, an amplified polynucleotide is at least about 16 nucleotides in length. More typically, an amplified polynucleotide is at least about 20 nucleotides in length. In one embodiment of the invention, an amplified polynucleotide is at least about 30 nucleotides in length. In another embodiment of the invention, an amplified polynucleotide is at least about 32, 40, 45, 50, or 60 nucleotides in length. In yet another embodiment of the invention, an amplified polynucleotide is at least about 100, 200, 300, 400, or 500 nucleotides in length. While the total length of an amplified polynucleotide of the invention can be as long as an exon, an intron or the entire gene where the SNP of interest resides, an amplified product is typically up to about 1,000 nucleotides in length (although certain amplification methods may generate amplified products greater than 1000 nucleotides in length). In another embodiment, an amplified polynucleotide is not greater than about 600-700 nucleotides in length. It is understood that irrespective of the length of an amplified polynucleotide, a SNP of interest may be located anywhere along its sequence.

In a specific embodiment of the invention, the amplified product is at least about 201 nucleotides in length, comprises one of SNPs shown in the figures. Such a product may have additional sequences on its 5' end or 3' end or both. In another embodiment, the amplified product is about 101 nucleotides in length, and it contains a SNP disclosed herein. The SNP may be located at the middle of the amplified product (e.g. at position 101 in an amplified product that is 201 nucleotides in length, or at position 51 in an amplified product that is 101 nucleotides in length), or within 1, 2, 3, 4, 5, 6, 7, 8, 9, 10, 12, 15, or 20 nucleotides from the middle of the amplified product (however, as indicated above, the SNP of interest may be located anywhere along the length of the amplified product).

Nucleic acid molecules are described that comprise, consist of, or consist essentially of one or more polynucleotide sequences that contain one or more SNPs disclosed herein, complements thereof, and SNP-containing fragments thereof.

Embodiments of the present invention further provide nucleic acid molecules that comprise any of the nucleotide sequences described. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A brief description of how various types of these nucleic acid molecules can be readily made and isolated is provided below, and such techniques are well known to those of ordinary skill in the art (Sambrook and Russell, 2000, Molecular Cloning: A Laboratory Manual, Cold Spring Harbor Press, NY).

The nucleic acid molecules can encode mature proteins plus additional amino or carboxyl-terminal amino acids or both, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production. As generally is the case in situ, the additional amino acids may be processed away from the mature protein by cellular enzymes.

Thus, the nucleic acid molecules include, but are not limited to, nucleic acid molecules having a sequence encoding a peptide alone, a sequence encoding a mature peptide and additional coding sequences such as a leader or secretory sequence (e.g., a pre-pro or pro-protein sequence), a sequence encoding a mature peptide with or without additional coding sequences, plus additional non-coding sequences, for example introns and non-coding 5' and 3' sequences such as transcribed but untranslated sequences that play a role in, for example, transcription, mRNA processing (including splicing and polyadenylation signals), ribosome binding, and/or stability of mRNA. In addition, the nucleic acid molecules may be fused to heterologous marker sequences encoding, for example, a peptide that facilitates purification.

Nucleic acid molecules can be in the form of RNA, such as mRNA, or in the form DNA, including cDNA and genomic DNA, which may be obtained, for example, by molecular cloning or produced by chemical synthetic techniques or by a combination thereof. Furthermore, nucleic acid molecules, particularly SNP detection reagents such as probes and primers, can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art (see, e.g., Corey, "Peptide nucleic acids: expanding the scope of nucleic acid recognition", Trends Biotechnol. 1997 June; 15(6):224-9, and Hyrup et al., "Peptide nucleic acids (PNA): synthesis, properties and potential applications", Bioorg Med. Chem. 1996 January; 4(1):5-23). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System, and the sequence information provided herein.

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more SNPs identified herein. Furthermore, kits/systems (such as beads, arrays, etc.) that include these analogs are also encompassed by the present invention. For example, PNA oligomers that are based on the polymorphic sequences of the present invention are specifically contemplated. PNA oligomers are analogs of DNA in which the phosphate backbone is replaced with a peptide-like backbone (Lagriffoul et al., Bioorganic & Medicinal Chemistry Letters, 4: 1081-1082 (1994), Petersen et al., Bioorganic & Medicinal Chemistry Letters, 6: 793-796 (1996), Kumar et al., Organic Letters 3(9): 1269-1272 (2001), WO96/04000). PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

Additional examples of nucleic acid modifications that improve the binding properties and/or stability of a nucleic acid include the use of base analogs such as inosine, intercalators (U.S. Pat. No. 4,835,263) and the minor groove binders (U.S. Pat. No. 5,801,115). Thus, references herein to nucleic acid molecules, SNP-containing nucleic acid molecules, SNP detection reagents (e.g., probes and primers), oligonucleotides/polynucleotides include PNA oligomers and other nucleic acid analogs. Other examples of nucleic acid analogs and alternative/modified nucleic acid chemistries known in the art are described in Current Protocols in Nucleic Acid Chemistry, John Wiley & Sons, N.Y. (2002).

The present invention further provides nucleic acid molecules that encode fragments of the variant polypeptides disclosed herein as well as nucleic acid molecules that encode obvious variants of such variant polypeptides. Such nucleic acid molecules may be naturally occurring, such as paralogs (different locus) and orthologs (different organism), or may be constructed by recombinant DNA methods or by chemical synthesis. Non-naturally occurring variants may be made by mutagenesis techniques, including those applied to nucleic acid molecules, cells, or organisms. Accordingly, the variants can contain nucleotide substitutions, deletions, inversions and insertions (in addition to the SNPs disclosed herein). Variation can occur in either or both the coding and non-coding regions. The variations can produce conservative and/or non-conservative amino acid substitutions.

Further variants of the nucleic acid molecules disclosed herein, such as naturally occurring allelic variants (as well as orthologs and paralogs) and synthetic variants produced by mutagenesis techniques, can be identified and/or produced using methods well known in the art. Such further variants can comprise a nucleotide sequence that shares at least 70-80%, 80-85%, 85-90%, 91%, 92%, 93%, 94%, 95%, 96%, 97%, 98%, or 99% sequence identity with a nucleic acid sequence disclosed herein (or a fragment thereof) and that includes a novel SNP allele disclosed herein. Further, variants can comprise a nucleotide sequence that encodes a polypeptide that shares at least 70-80%, 80-85%, 85-90%, 91%, 92%, 93%, 94%, 95%, 96%, 97%, 98%, or 99% sequence identity with a polypeptide sequence disclosed herein (or a fragment thereof) and that includes a novel SNP allele disclosed herein. Thus, an aspect of the present invention that is specifically contemplated are isolated nucleic acid molecules that have a certain degree of sequence variation compared with the sequences shown herein, but that contain a novel SNP allele disclosed herein. In other words, as long as an isolated nucleic acid molecule contains a novel SNP allele disclosed herein, other portions of the nucleic acid molecule that flank the novel SNP allele can vary to some degree from the specific transcript, genomic, and context sequences referred to and shown herein, and can encode a polypeptide that varies to some degree from the specific polypeptide sequences referred to herein.

To determine the percent identity of two amino acid sequences or two nucleotide sequences of two molecules that share sequence homology, the sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In some embodiments, the percent identity between two amino acid sequences is determined using the Needleman and Wunsch algorithm (J. Mol. Biol. (48):444-453 (1970)) which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

In yet another embodiment, the percent identity between two nucleotide sequences is determined using the GAP program in the GCG software package (Devereux, J., et al., Nucleic Acids Res. 12(1):387 (1984)), using a NWSgapdna CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12, and a gap penalty of 4.

The nucleotide and amino acid sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215:403-10 (1990)). BLAST nucleotide searches can be performed with the NTBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used. In addition to BLAST, examples of other search and sequence comparison programs used in the art include, but are not limited to, FASTA (Pearson, Methods Mol. Biol. 25, 365-389 (1994)) and KERR (Dufresne et al., Nat Biotechnol 2002 December; 20(12):1269-71). For further information regarding bioinformatics techniques, see Current Protocols in Bioinformatics, John Wiley & Sons, Inc., N.Y.

The present invention further provides non-coding fragments of the nucleic acid molecules disclosed herein. Non-coding fragments include, but are not limited to, promoter sequences, enhancer sequences, intronic sequences, 5' untranslated regions (UTRs), 3' untranslated regions, gene modulating sequences and gene termination sequences. Such fragments are useful, for example, in controlling heterologous gene expression and in developing screens to identify gene-modulating agents.

SNP Detection Reagents

A "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a probe that hybridizes to a target nucleic acid containing one or more of the SNPs referred to herein. In one embodiment, such a probe can differentiate between nucleic acids having a particular nucleotide (allele) at a target SNP position from other nucleic acids that have a different nucleotide at the same target SNP position. In addition, a detection reagent may hybridize to a specific region 5' and/or 3' to a SNP position, particularly a region corresponding to the context sequences referred to herein. Another example of a detection reagent is a primer that acts as an initiation point of nucleotide extension along a complementary strand of a target polynucleotide. The SNP sequence information provided herein is also useful for designing primers, e.g. allele-specific primers, to amplify (e.g., using PCR) any SNP of the present invention.

In one embodiment of the invention, a SNP detection reagent is an isolated or synthetic DNA or RNA polynucleotide probe or primer or PNA oligomer, or a combination of DNA, RNA and/or PNA, that hybridizes to a segment of a target nucleic acid molecule containing a SNP identified herein. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 55, 60, 65, 70, 80, 90, 100, 120 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

Other primer and probe sequences can readily be determined using the transcript sequences, genomic sequences, and SNP context sequences disclosed. It will be apparent to one of skill in the art that such primers and probes are directly useful as reagents for genotyping the SNPs of the present invention, and can be incorporated into any kit/system format.

In order to produce a probe or primer specific for a target SNP-containing sequence, the gene/transcript and/or context sequence surrounding the SNP of interest is typically examined using a computer algorithm that starts at the 5' or at the 3' end of the nucleotide sequence. Typical algorithms will then identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

A primer or probe is typically at least about 8 nucleotides in length. In one embodiment, a primer or a probe is at least about 10 nucleotides in length. In another embodiment, a primer or a probe is at least about 12 nucleotides in length. In another embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific embodiment, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length (see the section below entitled "SNP Detection Kits and Systems").

For analyzing SNPs, it may be appropriate to use oligonucleotides specific for alternative SNP alleles. Such oligonucleotides that detect single nucleotide variations in target sequences may be referred to by such terms as "allele-specific oligonucleotides", "allele-specific probes", or "allele-specific primers." The design and use of allele-specific probes for analyzing polymorphisms is described in, e.g., Mutation Detection A Practical Approach, ed. Cotton et al. Oxford University Press, 1998; Saiki et al, Nature 324, 163-166 (1986); Dattagupta, EP235,726; and Saiki, WO 89/11548.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: prehybridization with a solution containing 5× standard saline phosphate EDTA (SSPE), 0.5% NaDodSO$_4$ (SDS) at 55° C., and incubating probe with target nucleic acid molecules in the same solution at the same temperature, followed by washing with a solution containing 2×SSPE, and 0.1% SDS at 55° C. or room temperature.

Moderate stringency hybridization conditions may be used for allele-specific primer extension reactions with a solution containing, e.g., about 50 mM KCl at about 46° C. Alternatively, the reaction may be carried out at an elevated temperature such as 60° C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

In another embodiment, a probe or primer may be designed to hybridize to a segment of target DNA such that the SNP aligns with either the 5' most end or the 3' most end of the probe or primer. In a specific embodiment that is particularly suitable for use in a oligonucleotide ligation assay (U.S. Pat. No. 4,988,617), the 3' most nucleotide of the probe aligns with the SNP position in the target sequence.

Oligonucleotide probes and primers may be prepared by methods well known in the art.

Chemical synthetic methods include, but are limited to, the phosphotriester method described by Narang et al., 1979, Methods in Enzymology 68:90; the phosphodiester method described by Brown et al., 1979, Methods in Enzymology 68:109, the diethylphosphoamidate method described by Beaucage et al., 1981, Tetrahedron Letters 22:1859; and the solid support method described in U.S. Pat. No. 4,458,066.

Allele-specific probes are often used in pairs (or, less commonly, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position. Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res. 17 2427-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456). This PCR-based assay can be utilized as part of the TaqMan assay, described below.

In a specific embodiment of the invention, a primer contains a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In another embodiment, the mismatched nucleotide in the primer is the second from the last nucleotide at the 3'-most position of the primer. In another embodiment, the mismatched nucleotide in the primer is the last nucleotide at the 3'-most position of the primer.

In another embodiment, a SNP detection reagent is labeled with a fluorogenic reporter dye that emits a detectable signal. While the a common reporter dye is a fluorescent dye, any reporter dye that can be attached to a detection reagent such as an oligonucleotide probe or primer is suitable. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210, 015 and 5,538,848) or Molecular Beacon probe (U.S. Pat. Nos. 5,118,801 and 5,312,728), or other stemless or linear beacon probe (Livak et al., 1995, PCR Method Appl. 4:357-362; Tyagi et al., 1996, Nature Biotechnology 14: 303-308; Nazarenko et al., 1997, Nucl. Acids Res. 25:2516-2521; U.S. Pat. Nos. 5,866,336 and 6,117,635).

The detection reagents may also contain other labels, including but not limited to, biotin for streptavidin binding, hapten for antibody binding, and oligonucleotide for binding to another complementary oligonucleotide such as pairs of zipcodes.

Also contemplated are reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the 3'-most end of the primer extension product, and in which the ddNTP is a nucleotide of a SNP disclosed herein, is a composition that is specifically contemplated). Thus, reagents that bind to a nucleic acid molecule in a region adjacent to a SNP site and that are used for assaying the SNP site, even though the bound sequences do not necessarily include the SNP site itself, are also contemplated.

SNP Detection Kits and Systems

A person skilled in the art will recognize that, based on the SNP and associated sequence information disclosed herein, detection reagents can be developed and used to assay any SNP of the present invention individually or in combination, and such detection reagents can be readily incorporated into one of the established kit or system formats which are well known in the art. The terms "kits" and "systems", as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In one embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000 (or any other number in-between) or substantially all of the SNPs shown herein.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics", Biotechnol Annu Rev. 2002; 8:85-101; Sosnowski et al., "Active microelectronic array system for DNA hybridization, genotyping and pharmacogenomic applications", Psychiatr Genet. 2002 December; 12(4):181-92; Heller, "DNA microarray technology: devices, systems, and applications", Annu Rev Biomed Eng. 2002; 4:129-53. Epub 2002 Mar. 22; Kolchinsky et al., "Analysis of SNPs and other genomic variations using gel-based chips", Hum. Mutat. 2002 April; 19(4):343-60; and McGall et al., "High-density genechip oligonucleotide probe arrays", Adv Biochem Eng Biotechnol. 2002; 77:21-42.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of a gene/transcript or target SNP site, sequential polynucleotides that cover the full-length sequence of a gene/transcript; or unique polynucleotides selected from particular areas along the length of a target gene/transcript sequence, particularly areas corresponding to one or more SNPs disclosed herein. Polynucleotides used in the microarray or detection kit can be specific to a SNP or SNPs of interest (e.g., specific to a particular SNP allele at a target SNP site, or specific to particular SNP alleles at multiple different SNP sites), or specific to a polymorphic gene/transcript or genes/transcripts of interest.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section, and are well known to those skilled in the art and can be found in, for example, Current Protocols in Molecular Biology, John Wiley & Sons, N.Y. (1989), 6.3.1-6.3.6.

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In further embodiments, a nucleic acid array can comprise any number of probes, in which at least one probe is capable of detecting one or more SNPs disclosed herein, and sequences complementary thereto, said probe comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a novel SNP allele disclosed herein. In some embodiments, the nucleotide complementary to the SNP site is within 5, 4, 3, 2, or 1 nucleotide from the center of the probe, more preferably at the center of said probe.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, V, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present invention provides methods of identifying the SNPs disclosed herein in a test sample. Such methods typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. One skilled in the art will recognize that any one of the commonly available hybridization, amplification and array assay formats can readily be adapted to detect the SNPs disclosed herein.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM™ 6700 sample preparation system, and Roche Molecular Systems' COBAS AmpliPrep System.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include microfluidic devices known in the art (see, e.g., Weigl et al., "Lab-on-a-chip for drug development", Adv Drug Deliv Rev. 2003 Feb. 24; 55(3):349-77). In such microfluidic devices, the containers may be referred to as, for example, microfluidic "compartments", "chambers", or "channels".

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention. One example of a microfluidic system is disclosed in U.S. Pat. No. 5,589,136, which describes the integration of PCR amplification and capillary electrophoresis in chips. Exemplary microfluidic systems comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micromachined channels and to change the liquid flow rate for pumping across different sections of the microchip. See, for example, U.S. Pat. No. 6,153,073, Dubrow et al., and U.S. Pat. No. 6,156,181, Parce et al.

For genotyping SNPs, an exemplary microfluidic system may integrate, for example, nucleic acid amplification, primer extension, capillary electrophoresis, and a detection method such as laser induced fluorescence detection. In a first step of an exemplary process for using such an exemplary system, nucleic acid samples are amplified, preferably by PCR. Then, the amplification products are subjected to automated primer extension reactions using ddNTPs (specific fluorescence for each ddNTP) and the appropriate oligonucleotide primers to carry out primer extension reactions which hybridize just upstream of the targeted SNP. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

Uses of Nucleic Acid Molecules

The nucleic acid molecules of the present invention have a variety of uses, especially in the identification of humans at risk of drug overdose or underdose symptoms. For example, the nucleic acid molecules are useful as hybridization probes, such as for genotyping SNPs in messenger RNA, transcript, cDNA, genomic DNA, amplified DNA or other nucleic acid molecules, and for isolating full-length cDNA and genomic clones encoding the variant peptides disclosed herein as well as their orthologs.

A probe can hybridize to any nucleotide sequence along the entire length of a nucleic acid molecule referred to herein. Preferably, a probe of the present invention hybridizes to a region of a target sequence that encompasses a SNP position indicated herein. More preferably, a probe hybridizes to a SNP-containing target sequence in a sequence-specific manner such that it distinguishes the target sequence from other nucleotide sequences which vary from the target sequence only by which nucleotide is present at the SNP site. Such a probe is particularly useful for detecting the presence of a SNP-containing nucleic acid in a test sample, or for determining which nucleotide (allele) is present at a particular SNP site (i.e., genotyping the SNP site).

A nucleic acid hybridization probe may be used for determining the presence, level, form, and/or distribution of nucleic acid expression. The nucleic acid whose level is determined can be DNA or RNA. Accordingly, probes specific for the SNPs described herein can be used to assess the presence, expression and/or gene copy number in a given cell, tissue, or organism. These uses are relevant for diagnosis of disorders involving an increase or decrease in gene expression relative to normal levels. In vitro techniques for detection of mRNA include, for example, Northern blot hybridizations and in situ hybridizations. In vitro techniques for detecting DNA include Southern blot hybridizations and in situ hybridizations (Sambrook and Russell, 2000, Molecular Cloning: A Laboratory Manual, Cold Spring Harbor Press, Cold Spring Harbor, N.Y.).

Probes can be used as part of a diagnostic test kit for identifying cells or tissues in which a variant protein is expressed, such as by measuring the level of a variant protein-encoding nucleic acid (e.g., mRNA) in a sample of cells from a subject or determining if a polynucleotide contains a SNP of interest.

Thus, the nucleic acid molecules of the invention can be used as hybridization probes to detect the SNPs disclosed herein, thereby determining whether an individual with the polymorphisms is at risk for drug overdose or underdose symptoms or has developed early stage drug overdose or underdose symptoms. Detection of a SNP associated with a disease phenotype provides a diagnostic tool for an active disease and/or genetic predisposition to the disease.

Furthermore, the nucleic acid molecules of the invention are therefore useful for detecting a gene which contains a SNP disclosed herein and/or products of such genes, such as expressed mRNA transcript molecules, and are thus useful for detecting gene expression. The nucleic acid molecules can optionally be implemented in, for example, an array or kit format for use in detecting gene expression.

The nucleic acid molecules of the invention are also useful as primers to amplify any given region of a nucleic acid molecule, particularly a region containing a SNP identified in herein.

The nucleic acid molecules of the invention are also useful for constructing recombinant vectors (described in greater detail below). Such vectors include expression vectors that express a portion of, or all of, any of the variant peptide sequences referred to herein. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced SNPs.

The nucleic acid molecules of the invention are also useful for expressing antigenic portions of the variant proteins, particularly antigenic portions that contain a variant amino acid sequence (e.g., an amino acid substitution) caused by a SNP disclosed in herein.

The nucleic acid molecules of the invention are also useful for constructing vectors containing a gene regulatory region of the nucleic acid molecules of the present invention.

The nucleic acid molecules of the invention are also useful for designing ribozymes corresponding to all, or a part, of an mRNA molecule expressed from a SNP-containing nucleic acid molecule described herein.

The nucleic acid molecules of the invention are also useful for constructing host cells expressing a part, or all, of the nucleic acid molecules and variant peptides.

The nucleic acid molecules of the invention are also useful for constructing transgenic animals expressing all, or a part, of the nucleic acid molecules and variant peptides. The production of recombinant cells and transgenic animals having nucleic acid molecules which contain the SNPs disclosed herein allow, for example, effective clinical design of treatment compounds and dosage regimens.

The nucleic acid molecules of the invention are also useful in assays for drug screening to identify compounds that, for example, modulate nucleic acid expression.

The nucleic acid molecules of the invention are also useful in gene therapy in patients whose cells have aberrant gene expression. Thus, recombinant cells, which include a patient's cells that have been engineered ex vivo and returned to the patient, can be introduced into an individual where the recombinant cells produce the desired protein to treat the individual.

SNP Genotyping Methods

The process of determining which specific nucleotide (i.e., allele) is present at each of one or more SNP positions, such as a SNP position in a nucleic acid molecule disclosed herein, is referred to as SNP genotyping. The present invention provides methods of SNP genotyping, such as for use in identifying humans at risk of drug overdose or underdose symptoms, or not at risk, or for treatment, or determining responsiveness to a form of treatment, or in genome mapping or SNP association analysis, etc.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al., "Single nucleotide polymorphism genotyping: biochemistry, protocol, cost and throughput", Pharmacogenomics J. 2003; 3(2):77-96; Kwok et al., "Detection of single nucleotide polymorphisms", Curr Issues Mol Biol. 2003 April; 5(2): 43-60; Shi, "Technologies for individual genotyping: detection of genetic polymorphisms in drug targets and disease genes", Am J Pharmacogenomics. 2002; 2(3): 197-205; and Kwok, "Methods for genotyping single nucleotide polymorphisms", Annu Rev Genomics Hum Genet 2001; 2:235-58. Exemplary techniques for high-throughput SNP genotyping are described in Marnellos, "High-throughput SNP analysis for genetic association studies", Curr Opin Drug Discov Devel. 2003 May; 6(3):317-21. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA duplexes (Myers et al., Science 230:1242 (1985); Cotton et al., PNAS 85:4397 (1988); and Saleeba et al., Meth. Enzymol. 217:286-295 (1992)), comparison of the electrophoretic mobility of variant and wild type nucleic acid molecules (Orita et al., PNAS 86:2766 (1989); Cotton et al., Mutat. Res. 285:125-144 (1993); and Hayashi et al., Genet. Anal. Tech. Appl. 9:73-79 (1992)), and assaying the movement of polymorphic or wild-type fragments in polyacrylamide gels containing a gradient of denaturant using denaturing gradient gel electrophoresis (DGGE) (Myers et al., Nature 313:495 (1985)). Sequence variations at specific locations can also be assessed by nuclease protection assays such as RNase and S1 protection or chemical cleavage methods.

In a preferred embodiment, SNP genotyping is performed using the TaqMan assay, which is also known as the 5' nuclease assay (U.S. Pat. Nos. 5,210,015 and 5,538,848). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the SNPs of the present invention are useful in diagnostic assays for CHD, and in particular drug overdose or underdose or underdose symptoms and related pathologies, and can be readily incorporated into a kit format. The present invention also includes modifications of the Taqman assay well known in the art such as the use of Molecular Beacon probes (U.S. Pat. Nos. 5,118,801 and 5,312,728) and other variant formats (U.S. Pat. Nos. 5,866,336 and 6,117,635).

Another preferred method for genotyping the SNPs of the present invention is the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of OLA: U.S. Pat. Nos. 6,027,889, 6,268,148, 5,494,810, 5,830,711, and 6,054,564 describe OLA strategies for performing SNP detection; WO 97/31256 and WO 00/56927 describe OLA strategies for performing SNP detection using universal arrays, wherein a zipcode sequence can be introduced into one of the hybridization probes, and the resulting product, or amplified product, hybridized to a universal zip code array; U.S. application Ser. Nos. 01/17329 (and 09/584,905) describes OLA (or LDR) followed by PCR, wherein zipcodes are incorporated into OLA probes, and amplified PCR products are determined by electrophoretic or universal zipcode array readout; U.S. applications 60/427,818, 60/445,636, and 60/445,494 describe SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization—Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

Typically, the primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position. For further information regarding the use of primer extension assays in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry", Rapid Commun Mass Spectrom. 2003; 17(11): 1195-202.

The following references provide further information describing mass spectrometry-based methods for SNP genotyping: Bocker, "SNP and mutation discovery using basespecific cleavage and MALDI-TOF mass spectrometry", Bioinformatics. 2003 July; 19 Suppl 1:144-153; Storm et al., "MALDI-TOF mass spectrometry-based SNP genotyping", Methods Mol. Biol. 2003; 212:241-62; Jurinke et al., "The use of Mass ARRAY technology for high throughput genotyping," Adv Biochem Eng Biotechnol. 2002; 77:57-74; and Jurinke et al., "Automated genotyping using the DNA MassArray technology," Methods Mol. Biol. 2002; 187:179-92.

SNPs can also be scored by direct DNA sequencing. A variety of automated sequencing procedures can be utilized ((1995) Biotechniques 19:448), including sequencing by mass spectrometry (see, e.g., PCT International Publication No. WO94/16101; Cohen et al., Adv. Chromatogr. 36:127-162 (1996); and Griffin et al., Appl. Biochem. Biotechnol. 38:147-159 (1993)). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730 x1 DNA Analyzers (Foster City, Calif.), is commonly used in the art for automated sequencing.

Other methods that can be used to genotype the SNPs of the present invention include single-strand conformational polymorphism (SSCP), and denaturing gradient gel electrophoresis (DGGE) (Myers et al., Nature 313:495 (1985)). SSCP identifies base differences by alteration in electrophoretic migration of single stranded PCR products, as described in Orita et al., Proc. Nat. Acad. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel (Erlich, ed., PCR Technology, Principles and Applications for DNA Amplification, W.H. Freeman and Co, New York, 1992, Chapter 7).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

SNP genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described below. Examples of such applications include, but are not limited to, SNP-disease association analysis, disease predisposition screening, disease diagnosis, disease prognosis, disease progression monitoring, determining therapeutic strategies based on an individual's genotype ("pharmacogenomics"), developing therapeutic agents based on SNP genotypes associated with a disease or likelihood of responding to a drug, stratifying a patient population for clinical trial for a treatment regimen, predicting the likelihood that an individual will experience toxic side effects from a therapeutic agent, and human identification applications such as forensics.

Analysis of Genetic Association Between SNPs and Phenotypic Traits

SNP genotyping for disease diagnosis, disease predisposition screening, disease prognosis, determining drug responsiveness (pharmacogenomics), drug toxicity screening, and other uses described herein, typically relies on initially establishing a genetic association between one or more specific SNPs and the particular phenotypic traits of interest.

Different study designs may be used for genetic association studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

In both types of observational studies, there may be potential confounding factors that should be taken into consideration. Confounding factors are those that are associated with both the real cause(s) of the disease and the disease itself, and they include demographic information such as age, gender, ethnicity as well as environmental factors. When confounding factors are not matched in cases and controls in a study, and are not controlled properly, spurious association results can arise. If potential confounding factors are identified, they should be controlled for by analysis methods explained below.

In a genetic association study, the cause of interest to be tested is a certain allele or a SNP or a combination of alleles or a haplotype from several SNPs. Thus, tissue specimens (e.g., whole blood) from the sampled individuals may be collected and genomic DNA genotyped for the SNP(s) of interest. In addition to the phenotypic trait of interest, other information such as demographic (e.g., age, gender, ethnicity, etc.), clinical, and environmental information that may influence the outcome of the trait can be collected to further characterize and define the sample set. In many cases, these factors are known to be associated with diseases and/or SNP allele frequencies. There are likely gene-environment and/or gene-gene interactions as well. Analysis methods to address gene-environment and gene-gene interactions (for example, the effects of the presence of both susceptibility alleles at two different genes can be greater than the effects of the individual alleles at two genes combined) are discussed below.

After all the relevant phenotypic and genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively. To ensure genotyping quality, Hardy-Weinberg disequilibrium tests can be performed on cases and controls separately. Significant deviation from Hardy-Weinberg equilibrium (HWE) in both cases and controls for individual markers can be indicative of genotyping errors. If HWE is violated in a majority of markers, it is indicative of population substructure that should be further investigated. Moreover, Hardy-Weinberg disequilibrium in cases only can indicate genetic association of the markers with the disease (Genetic Data Analysis, Weir B., Sinauer (1990)).

To test whether an allele of a single SNP is associated with the case or control status of a phenotypic trait, one skilled in the art can compare allele frequencies in cases and controls. Standard chi-squared tests and Fisher exact tests can be carried out on a 2×2 table (2 SNP alleles×2 outcomes in the categorical trait of interest). To test whether genotypes of a SNP are associated, chi-squared tests can be carried out on a 3×2 table (3 genotypes×2 outcomes). Score tests are also carried out for genotypic association to contrast the three genotypic frequencies (major homozygotes, heterozygotes and minor homozygotes) in cases and controls, and to look for trends using 3 different modes of inheritance, namely dominant (with contrast coefficients 2, −1, −1), additive (with contrast coefficients 1, 0, −1) and recessive (with contrast coefficients 1, 1, −2). Odds ratios for minor versus major alleles, and odds ratios for heterozygote and homozygote variants versus the wild type genotypes are calculated with the desired confidence limits, usually 95%.

In order to control for confounders and to test for interaction and effect modifiers, stratified analyses may be performed using stratified factors that are likely to be confounding, including demographic information such as age, ethnicity, and gender, or an interacting element or effect modifier, such as a known major gene (e.g., APOE for Alzheimer's disease or HLA genes for autoimmune diseases), or environmental factors such as smoking in lung cancer. Stratified association tests may be carried out using Cochran-Mantel-Haenszel tests that take into account the ordinal nature of genotypes with 0, 1, and 2 variant alleles. Exact tests by StatXact may also be performed when computationally possible. Another way to adjust for confounding effects and test for interactions is to perform stepwise multiple logistic regression analysis using statistical packages such as SAS or R. Logistic regression is a model-building technique in which the best fitting and most parsimonious model is built to describe the relation between the dichotomous outcome (for instance, getting a certain disease or not) and a set of independent variables (for instance, genotypes of different associated genes, and the associated demographic and environmental factors). The most common model is one in which the logit transformation of the odds ratios is expressed as a linear combination of the variables (main effects) and their cross-product terms (interactions) (Applied Logistic Regression, Hosmer and Lemeshow, Wiley (2000)). To test whether a certain variable or interaction is significantly associated with the outcome, coefficients in the model are first estimated and then tested for statistical significance of their departure from zero.

In addition to performing association tests one marker at a time, haplotype association analysis may also be performed to study a number of markers that are closely linked together. Haplotype association tests can have better power than genotypic or allelic association tests when the tested markers are not the disease-causing mutations themselves but are in linkage disequilibrium with such mutations. The test will even be more powerful if the disease is indeed caused by a combination of alleles on a haplotype (e.g., APOE is a haplotype formed by 2 SNPs that are very close to each other). In order to perform haplotype association effectively, marker-marker linkage disequilibrium measures, both D' and r.sup.2, are typically calculated for the markers within a gene to elucidate the haplotype structure. Recent studies (Daly et al, Nature Genetics, 29, 232-235, 2001) in linkage disequilibrium indicate that SNPs within a gene are organized in block pattern, and a high degree of linkage disequilibrium exists within blocks and very little linkage disequilibrium exists between blocks. Haplotype association with the disease status can be performed using such blocks once they have been elucidated.

Haplotype association tests can be carried out in a similar fashion as the allelic and genotypic association tests. Each haplotype in a gene is analogous to an allele in a multi-allelic marker. One skilled in the art can either compare the haplotype frequencies in cases and controls or test genetic association with different pairs of haplotypes. It has been proposed (Schaid et al, Am. J. Hum. Genet., 70, 425-434, 2002) that score tests can be done on haplotypes using the program "haplo.score." In that method, haplotypes are first inferred by EM algorithm and score tests are carried out with a generalized linear model (GLM) framework that allows the adjustment of other factors.

An important decision in the performance of genetic association tests is the determination of the significance level at which significant association can be declared when the P value of the tests reaches that level. In an exploratory analysis where positive hits will be followed up in subsequent confirmatory testing, an unadjusted P value<0.2 (a significance level on the lenient side), for example, may be used for generating hypotheses for significant association of a SNP with certain phenotypic characteristics of a disease. It is preferred that a p-value<0.05 (a significance level traditionally used in the art) is achieved in order for a SNP to be considered to have an association with a disease. It is more preferred that a p-value<0.01 (a significance level on the stringent side) is achieved for an association to be declared. When hits are followed up in confirmatory analyses in more samples of the same source or in different samples from different sources, adjustment for multiple testing will be performed as to avoid excess number of hits while maintaining the experiment-wide error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

In replication studies using samples from different populations after statistically significant markers have been identified in the exploratory stage, meta-analyses can then be performed by combining evidence of different studies (Modern Epidemiology, Lippincott Williams & Wilkins, 1998, 643-673). If available, association results known in the art for the same SNPs can be included in the meta-analyses.

Since both genotyping and disease status classification can involve errors, sensitivity analyses may be performed to see how odds ratios and p-values would change upon various estimates on genotyping and disease classification error rates.

It has been well known that subpopulation-based sampling bias between cases and controls can lead to spurious results in case-control association studies (Ewens and Spielman, Am. J. Hum. Genet. 62, 450-458, 1995) when prevalence of the disease is associated with different subpopulation groups. Such bias can also lead to a loss of statistical power in genetic association studies. To detect population stratification, Pritchard and Rosenberg (Pritchard et al. Am. J. Hum. Gen. 1999, 65:220-228) suggested typing markers that are unlinked to the disease and using results of association tests on those markers to determine whether there is any population stratification. When stratification is detected, the genomic control (GC) method as proposed by Devlin and Roeder (Devlin et al. Biometrics 1999, 55:997-1004) can be used to adjust for the inflation of test statistics due to population stratification. GC method is robust to changes in population structure levels as well as being applicable to DNA pooling designs (Devlin et al. Genet. Epidem. 20001, 21:273-284).

While Pritchard's method recommended using 15-20 unlinked microsatellite markers, it suggested using more than 30 biallelic markers to get enough power to detect population stratification. For the GC method, it has been shown (Bacanu et al. Am. J. Hum. Genet. 2000, 66:1933-1944) that about 60-70 biallelic markers are sufficient to estimate the inflation factor for the test statistics due to population stratification. Hence, 70 intergenic SNPs can be chosen in unlinked regions as indicated in a genome scan (Kehoe et al. Hum. Mol. Genet. 1999, 8:237-245).

Once individual risk factors, genetic or non-genetic, have been found for the predisposition to disease, the next step is to set up a classification/prediction scheme to predict the category (for instance, disease or no-disease) that an individual will be in depending on his genotypes of associated SNPs and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

Disease Diagnosis and Predisposition Screening

Information on association/correlation between genotypes and disease-related phenotypes can be exploited in several ways. For example, in the case of a highly statistically significant association between one or more SNPs with predisposition to a disease for which treatment is available, detection of such a genotype pattern in an individual may justify immediate administration of treatment, or at least the institution of regular monitoring of the individual. Detection of the susceptibility alleles associated with serious disease in a couple contemplating having children may also be valuable to the couple in their reproductive decisions. In the case of a weaker but still statistically significant association between a SNP and a human disease, immediate therapeutic intervention or monitoring may not be justified after detecting the susceptibility allele or SNP. Nevertheless, the subject can be motivated to begin simple life-style changes (e.g., diet, exercise) that can be accomplished at little or no cost to the individual but would confer potential benefits in reducing the risk of developing conditions for which that individual may have an increased risk by virtue of having the risk allele(s).

The SNP profiles of the invention may contribute to the development of drug overdose or underdose symptoms in an individual in different ways. Some polymorphisms occur within a protein coding sequence and contribute to disease phenotype by affecting protein structure. Other polymorphisms occur in noncoding regions but may exert phenotypic effects indirectly via influence on, for example, replication, transcription, and/or translation. A single SNP may affect more than one phenotypic trait. Likewise, a single phenotypic trait may be affected by multiple SNPs in different genes.

As used herein, the terms "diagnose," "diagnosis," and "diagnostics" include, but are not limited to any of the following: detection of drug overdose or underdose symptoms an individual may presently have, predisposition/susceptibility screening (i.e., determining the increased risk of an individual in developing drug overdose or underdose symptoms in the future, or determining whether an individual has a decreased risk of developing drug overdose or underdose symptoms in the future), determining a particular type or subclass of drug overdose or underdose symptoms in an individual known to have drug overdose or underdose symptoms or propensity, confirming or reinforcing a previously made diagnosis of drug overdose or underdose symptoms or propensity, pharmacogenomic evaluation of an individual to determine which therapeutic strategy that individual is most likely to positively respond to or to predict whether a patient is likely to respond to a particular treatment such as a particular drug, predicting whether a patient is likely to experience toxic effects from a particular treatment or therapeutic compound, and evaluating the future prognosis of an individual having drug overdose or underdose symptoms or propensity. Such diagnostic uses are based on the SNPs individually or in a unique combination or SNP haplotypes of the present invention.

Haplotypes are particularly useful in that, for example, fewer SNPs can be genotyped to determine if a particular genomic region harbors a locus that influences a particular phenotype, such as in linkage disequilibrium-based SNP association analysis.

Linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium." In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby.

Hence, genotyping one of the SNP sites will give almost the same information as genotyping the other SNP site that is in LD.

Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome.

For diagnostic purposes and similar uses, if a particular SNP site is found to be useful for diagnosing CHD (e.g., has a significant statistical association with the condition and/or is recognized as a causative polymorphism for the condition), then the skilled artisan would recognize that other SNP sites which are in LD with this SNP site would also be useful for diagnosing the condition. Thus, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., drug overdose or underdose symptoms or propensity) that is influenced by the causative SNP(s). Therefore, polymorphic markers that are in LD with causative polymorphisms are useful as diagnostic markers, and are particularly useful when the actual causative polymorphism(s) is/are unknown.

Examples of polymorphisms that can be in LD with one or more causative polymorphisms (and/or in LD with one or more polymorphisms that have a significant statistical association with a condition) and therefore useful for diagnosing the same condition that the causative/associated SNP(s) is used to diagnose, include other SNPs in the same gene, protein-coding, or mRNA transcript-coding region as the causative/associated SNP, other SNPs in the same exon or same intron as the causative/associated SNP, other SNPs in the same haplotype block as the causative/associated SNP, other SNPs in the same intergenic region as the causative/associated SNP, SNPs that are outside but near a gene (e.g., within 6 kb on either side, 5' or 3', of a gene boundary) that harbors a causative/associated SNP, etc. Such useful LD SNPs can be selected from among the SNPs disclosed herein, for example.

Linkage disequilibrium in the human genome is reviewed in: Wall et al., "Haplotype blocks and linkage disequilibrium in the human genome", Nat Rev Genet. 2003 August; 4(8):587-97; Garner et al., "On selecting markers for association studies: patterns of linkage disequilibrium between two and three diallelic loci", Genet Epidemiol. 2003 January; 24(1):57-67; Ardlie et al., "Patterns of linkage disequilibrium in the human genome", Nat Rev Genet. 2002 April; 3(4):299-309 (erratum in Nat Rev Genet 2002 July; 3(7): 566); and Remm et al., "High-density genotyping and linkage disequilibrium in the human genome using chromosome 22 as a model"; Curr Opin Chem Biol. 2002 February; 6(1):24-30; Haldane J B S (1919) The combination of linkage values, and the calculation of distances between the loci of linked factors. J Genet 8:299-309; Mendel, G. (1866) Versuche uber Pflanzen-Hybriden. Verhandlungen des naturforschenden Vereines in Brunn [Proceedings of the Natural History Society of Brunn]; Lewin B (1990) Genes IV. Oxford University Press, New York, USA; Hartl D L and Clark A G (1989) Principles of Population Genetics 2.sup.nd ed. Sinauer Associates, Inc. Sunderland, Mass., USA; Gillespie J H (2004) Population Genetics: A Concise Guide. 2.sup.nd ed. Johns Hopkins University Press. USA; Lewontin R C (1964) The interaction of selection and linkage. I. General considerations; heterotic models. Genetics 49:49-67; Hoel P G (1954) Introduction to Mathematical Statistics 2.sup.nd ed. John Wiley & Sons, Inc. New York, USA; Hudson R R (2001) Two-locus sampling distributions and their application. Genetics 159:1805-1817; Dempster A P, Laird N M, Rubin D B (1977) Maximum likelihood from incomplete data via the EM algorithm. J R Stat Soc 39:1-38; Excoffier L, Slatkin M (1995) Maximum-likelihood estimation of molecular haplotype frequencies in a diploid population. Mol Biol Evol 12(5):921-927; Tregouet D A, Escolano S, Tiret L, Mallet A, Golmard J L (2004) A new algorithm for haplotype-based association analysis: the Stochastic-EM algorithm. Ann Hum Genet 68(Pt 2):165-177; Long A D and Langley C H (1999) The power of association studies to detect the contribution of candidate genetic loci to variation in complex traits. Genome Research 9:720-731; Agresti A (1990) Categorical Data Analysis. John Wiley & Sons, Inc. New York, USA; Lange K (1997) Mathematical and Statistical Methods for Genetic Analysis. Springer-Verlag New York, Inc. New York, USA; The International HapMap Consortium (2003) The International HapMap Project. Nature 426:789-796; The International HapMap Consortium (2005) A haplotype map of the human genome. Nature 437:1299-1320; Thorisson G A, Smith A V, Krishnan L, Stein L D (2005), The International HapMap Project Web Site. Genome Research 15:1591-1593; McVean G, Spencer C C A, Chaix R (2005) Perspectives on human genetic variation from the HapMap project. PLoS Genetics 1(4): 413-418; Hirschhorn J N, Daly M J (2005) Genome-wide association studies for common diseases and complex traits. Nat Genet 6:95-108; Schrodi S J (2005) A probabilistic approach to large-scale association scans: a semi-Bayesian method to detect disease-predisposing alleles. SAGMB 4(1): 31; Wang W Y S, Barratt B J, Clayton D G, Todd J A (2005) Genome-wide association studies: theoretical and practical concerns. Nat Rev Genet 6:109-118. Pritchard J K, Przeworski M (2001) Linkage disequilibrium in humans: models and data. Am J Hum Genet 69:1-14.

As discussed above, one aspect of the present invention is the discovery that SNPs which are in certain LD distance with the interrogated SNP can also be used as valid markers for identifying an increased or decreased risks of having or developing drug overdose or underdose symptoms or propensity. As used herein, the term "interrogated SNP" refers to SNPs that have been found to be associated with an increased or decreased risk of disease using genotyping results and analysis, or other appropriate experimental method as exemplified in the working examples described in this application. As used herein, the term "LD SNP" refers to a SNP that has been characterized as a SNP associating with an increased or decreased risk of diseases due to their being in LD with the "interrogated SNP" under the methods of calculation described in the application. Below, applicants describe the methods of calculation with which one of ordinary skilled in the art may determine if a particular SNP is in LD with an interrogated SNP. The parameter $r^2$ is commonly used in the genetics art to characterize the extent of linkage disequilibrium between markers (Hudson, 2001). As used herein, the term "in LD with" refers to a particular SNP that is measured at above the threshold of a parameter such as $r^2$ with an interrogated SNP.

The contribution or association of particular SNPs and/or SNP haplotypes with disease phenotypes, such as drug overdose or underdose symptoms or propensity, enables the SNPs of the present invention to be used to develop superior diagnostic tests capable of identifying individuals who express a detectable trait, such as drug overdose or underdose symptoms or propensity, as the result of a specific genotype, or individuals whose genotype places them at an increased or decreased risk of developing a detectable trait at a subsequent time as compared to individuals who do not have that genotype. As described herein, diagnostics may be based on a single SNP or a group of SNPs. Combined detection of a plurality of SNPs (for example, 2, 3, 4, 5, 6, 7, 8, 9, 10, 11, 12, 13, 14, 15, 16, 17, 18, 19, 20, 24, 25, 30, 32, 48, 50, 64, 96, 100, or any other number in-between, or more, of the SNPs herein) typically increases the probability of an accurate diagnosis. To further increase the accuracy of diagnosis or predisposition screening, analysis of the SNPs of the present invention can be combined with that of other polymorphisms or other risk factors of drug overdose or underdose symptoms or propensity, such as disease symptoms, pathological characteristics, family history, diet, environmental factors or lifestyle factors.

It will, of course, be understood by practitioners skilled in the treatment or diagnosis of drug overdose or underdose symptoms or propensity that the present invention generally does not intend to provide an absolute identification of individuals who are at risk (or less at risk) of developing drug overdose or underdose symptoms or propensity, and/or pathologies related to such as drug overdose or underdose symptoms or propensity, but rather to indicate a certain increased (or decreased) degree or likelihood of developing the pathology based on statistically significant association results. However, this information is extremely valuable as it can be used to, for example, initiate preventive treatments or to allow an individual carrying one or more significant SNPs or SNP haplotypes to foresee warning signs such as minor clinical symptoms, or to have regularly scheduled physical exams to monitor for appearance of a condition in order to identify and begin treatment of the condition at an early stage. Particularly with diseases that are extremely debilitating or fatal if not treated on time, the knowledge of a potential predisposition, even if this predisposition is not absolute, would likely contribute in a very significant manner to treatment efficacy.

The diagnostic techniques of the present invention may employ a variety of methodologies to determine whether a test subject has a SNP or a SNP pattern associated with an increased or decreased risk of developing a detectable trait or whether the individual suffers from a detectable trait as a result of a particular polymorphism/mutation, including, for example, methods which enable the analysis of individual chromosomes for haplotyping, family studies, single sperm DNA analysis, or somatic hybrids. The trait analyzed using the diagnostics of the invention may be any detectable trait that is commonly observed in pathologies and disorders related to drug overdose or underdose symptoms or propensity.

Another aspect of the present invention relates to a method of determining whether an individual is at risk (or less at risk) of developing one or more traits or whether an individual expresses one or more traits as a consequence of possessing a particular trait-causing or trait-influencing allele. These methods generally involve obtaining a nucleic acid sample from an individual and assaying the nucleic acid sample to determine which nucleotide(s) is/are present at one or more SNP positions, wherein the assayed nucleotide(s) is/are indicative of an increased or decreased risk of developing the trait or indicative that the individual expresses the trait as a result of possessing a particular trait-causing or trait-influencing allele.

In another embodiment, the SNP detection reagents of the present invention are used to determine whether an individual has one or more SNP allele(s) affecting the level (e.g., the concentration of mRNA or protein in a sample, etc.) or pattern (e.g., the kinetics of expression, rate of decomposition, stability profile, Km, Vmax, etc.) of gene expression (collectively, the "gene response" of a cell or bodily fluid). Such a determination can be accomplished by screening for mRNA or protein expression (e.g., by using nucleic acid arrays, RT-PCR, TaqMan assays, or mass spectrometry), identifying genes having altered expression in an individual, genotyping SNPs disclosed herein that could affect the expression of the genes having altered expression (e.g., SNPs that are in and/or around the gene(s) having altered expression, SNPs in regulatory/control regions, SNPs in and/or around other genes that are involved in pathways that could affect the expression of the gene(s) having altered expression, or all SNPs could be genotyped), and correlating SNP genotypes with altered gene expression. In this manner, specific SNP alleles at particular SNP sites can be identified that affect gene expression.

Selecting Individualized Dosage

In some embodiments, the dose of one or more drugs administered to a patient is adjusted based on metabolizer status classification. For example, if a statin, like atorvastatin, lovastatin, pravastatin, or simvastatin, is administered in a range of 10-80 mg/day, a patient assigned to receive a low dose might receive 10-20 mg/day as an initial dose while a patient classified as likely to benefit from a high dose might be assigned an initial dose of 40-60 mg/day and a intermediate metabolizer might be assigned an initial dose of 20-40 mg/day. Adjustments to dosing could subsequently be made, as needed or at regular intervals, based on patient response to therapy.

Pharmacogenomics and Therapeutics/Drug Development

The present invention provides methods for assessing the pharmacogenomics of a subject harboring particular SNP alleles or haplotypes to a particular therapeutic agent or pharmaceutical compound, or to a class of such compounds. Pharmacogenomics deals with the roles which clinically significant hereditary variations (e.g., SNPs) play in the response to drugs due to altered drug disposition and/or abnormal action in affected persons. See, e.g., Roses, Nature 405, 857-865 (2000); Gould Rothberg, Nature Biotechnology 19, 209-211 (2001); Eichelbaum, Clin. Exp. Pharmacol. Physiol. 23(10-11):983-985 (1996); and Linder, Clin. Chem. 43(2):254-266 (1997). The clinical outcomes of these variations can result in severe toxicity of therapeutic drugs in certain individuals or therapeutic failure of drugs in certain individuals as a result of individual variation in metabolism. Thus, the SNP genotype of an individual can determine the way a therapeutic compound acts on the body or the way the body metabolizes the compound. For example, SNPs in drug metabolizing enzymes can affect the activity of these enzymes, which in turn can affect both the intensity and duration of drug action, as well as drug metabolism and clearance.

The discovery of SNPs in drug metabolizing enzymes, drug transporters, proteins for pharmaceutical agents, and other drug targets has explained why some patients do not obtain the expected drug effects, show an exaggerated drug effect, or experience serious toxicity from standard drug dosages. SNPs can be expressed in the phenotype of the extensive metabolizer and in the phenotype of the poor metabolizer. Accordingly, SNPs may lead to allelic variants of a protein in which one or more of the protein functions in one population are different from those in another population. SNPs and the encoded variant peptides thus provide targets to ascertain a genetic predisposition that can affect treatment modality. For example, in a ligand-based treatment, SNPs may give rise to amino terminal extracellular domains and/or other ligand-binding regions of a receptor that are more or less active in ligand binding, thereby affecting subsequent protein activation. Accordingly, ligand dosage would necessarily be modified to maximize the therapeutic effect within a given population containing particular SNP alleles or haplotypes.

As an alternative to genotyping, specific variant proteins containing variant amino acid sequences encoded by alternative SNP alleles could be identified. Thus, pharmacogenomic characterization of an individual permits the selection of effective compounds and effective dosages of such compounds for prophylactic or therapeutic uses based on the individual's SNP genotype, thereby enhancing and optimizing the effectiveness of the therapy. Furthermore, the production of recombinant cells and transgenic animals containing particular SNPs/haplotypes allow effective clinical design and testing of treatment compounds and dosage regimens. For example, transgenic animals can be produced that differ only in specific SNP alleles in a gene that is orthologous to a human disease susceptibility gene.

Pharmacogenomic uses of the SNPs of the present invention provide several significant advantages for patient care, particularly in treating drug overdose or underdose symptoms or propensity. Pharmacogenomic characterization of an individual, based on an individual's SNP genotype, can identify those individuals unlikely to respond to treatment with a particular medication and thereby allows physicians to avoid prescribing the ineffective medication to those individuals. On the other hand, SNP genotyping of an individual may enable physicians to select the appropriate medication and dosage regimen that will be most effective based on an individual's SNP genotype. This information increases a physician's confidence in prescribing medications and motivates patients to comply with their drug regimens. Furthermore, pharmacogenomics may identify patients predisposed to toxicity and adverse reactions to particular drugs or drug dosages. Adverse drug reactions lead to more than 100,000 avoidable deaths per year in the United States alone and therefore represent a significant cause of hospitalization and death, as well as a significant economic burden on the healthcare system (Pfost et. al., Trends in Biotechnology, August 2000.). Thus, pharmacogenomics based on the SNPs disclosed herein has the potential to both save lives and reduce healthcare costs substantially.

Pharmacogenomics in general is discussed further in Rose et al., "Pharmacogenetic analysis of clinically relevant genetic polymorphisms", Methods Mol Med. 2003; 85:225-37. Pharmacogenomics as it relates to Alzheimer's disease and other neurodegenerative disorders is discussed in Cacabelos, "Pharmacogenomics for the treatment of dementia", Ann Med. 2002; 34(5):357-79, Maimone et al., "Pharmacogenomics of neurodegenerative diseases", Eur J Pharmacol. 2001 Feb. 9; 413(1): 11-29, and Poirier, "Apolipoprotein E: a pharmacogenetic target for the treatment of Alzheimer's disease", Mol Diagn. 1999 December; 4(4): 335-41. Pharmacogenomics as it relates to cardiovascular disorders is discussed in Siest et al., "Pharmacogenomics of drugs affecting the cardiovascular system", Clin Chem Lab Med. 2003 April; 41(4):590-9, Mukherjee et al., "Pharmacogenomics in cardiovascular diseases", Prog Cardiovasc Dis. 2002 May-June; 44(6):479-98, and Mooser et al., "Cardiovascular pharmacogenetics in the SNP era", J Thromb Haemost. 2003 July; 1(7):1398-402. Pharmacogenomics as it relates to cancer is discussed in McLeod et al., "Cancer pharmacogenomics: SNPs, chips, and the individual patient", Cancer Invest. 2003; 21(4):630-40 and Watters et al., "Cancer pharmacogenomics: current and future applications", Biochim Biophys Acta. 2003 Mar. 17; 1603(2):99-111.

The SNPs of the present invention also can be used to identify novel therapeutic targets for drug overdose or underdose symptoms or propensity. For example, genes containing the disease-associated variants ("variant genes") or their products, as well as genes or their products that are directly or indirectly regulated by or interacting with these variant genes or their products, can be targeted for the development of therapeutics that, for example, treat the disease or prevent or delay disease onset. The therapeutics may be composed of, for example, small molecules, proteins, protein fragments or peptides, antibodies, nucleic acids, or their derivatives or mimetics which modulate the functions or levels of the target genes or gene products.

The SNP-containing nucleic acid molecules disclosed herein, and their complementary nucleic acid molecules, may be used as antisense constructs to control gene expression in cells, tissues, and organisms. Antisense technology is well established in the art and extensively reviewed in Antisense Drug Technology: Principles, Strategies, and Applications, Crooke (ed.), Marcel Dekker, Inc.: New York (2001). An antisense nucleic acid molecule is generally designed to be complementary to a region of mRNA expressed by a gene so that the antisense molecule hybridizes to the mRNA and thereby blocks translation of mRNA into protein. Various classes of antisense oligonucleotides are used in the art, two of which are cleavers and blockers. Cleavers, by binding to target RNAs, activate intracellular nucleases (e.g., RNaseH or RNase L) that cleave the target RNA. Blockers, which also bind to target RNAs, inhibit protein translation through steric hindrance of ribosomes. Exemplary blockers include peptide nucleic acids, morpholinos, locked nucleic acids, and methylphosphonates (see, e.g., Thompson, Drug Discovery Today, 7 (17): 912-917 (2002)). Antisense oligonucleotides are directly useful as therapeutic agents, and are also useful for determining and validating gene function (e.g., in gene knock-out or knock-down experiments).

Antisense technology is further reviewed in: Lavery et al., "Antisense and RNAi: powerful tools in drug target discovery and validation", Curr Opin Drug Discov Devel. 2003 July; 6(4):561-9; Stephens et al., "Antisense oligonucleotide therapy in cancer", Curr Opin Mol Ther. 2003 April; 5(2): 118-22; Kurreck, "Antisense technologies. Improvement through novel chemical modifications", Eur J. Biochem. 2003 April; 270(8): 1628-44; Dias et al., "Antisense oligonucleotides: basic concepts and mechanisms", Mol Cancer Ther. 2002 March; 1(5):347-55; Chen, "Clinical development of antisense oligonucleotides as anti-cancer therapeutics", Methods Mol Med. 2003; 75:621-36; Wang et al., "Antisense anticancer oligonucleotide therapeutics", Curr Cancer Drug Targets. 2001 November; 1(3):177-96; and Bennett, "Efficiency of antisense oligonucleotide drug discovery", Antisense Nucleic Acid Drug Dev. 2002 June; 12(3):215-24.

The SNPs of the present invention are particularly useful for designing antisense reagents that are specific for particular nucleic acid variants. Based on the SNP information disclosed herein, antisense oligonucleotides can be produced that specifically target mRNA molecules that contain one or more particular SNP nucleotides. In this manner, expression of mRNA molecules that contain one or more undesired polymorphisms (e.g., SNP nucleotides that lead to a defective protein such as an amino acid substitution in a catalytic domain) can be inhibited or completely blocked. Thus, antisense oligonucleotides can be used to specifically bind a particular polymorphic form (e.g., a SNP allele that encodes a defective protein), thereby inhibiting translation of this form, but which do not bind an alternative polymorphic form (e.g., an alternative SNP nucleotide that encodes a protein having normal function).

Antisense molecules can be used to inactivate mRNA in order to inhibit gene expression and production of defective proteins. Accordingly, these molecules can be used to treat a disorder, such as drug overdose or underdose symptoms, characterized by abnormal or undesired gene expression or expression of certain defective proteins. This technique can involve cleavage by means of ribozymes containing nucleotide sequences complementary to one or more regions in the mRNA that attenuate the ability of the mRNA to be translated. Possible mRNA regions include, for example, protein-coding regions and particularly protein-coding regions corresponding to catalytic activities, substrate/ligand binding, or other functional activities of a protein.

The SNPs of the present invention are also useful for designing RNA interference reagents that specifically target nucleic acid molecules having particular SNP variants. RNA interference (RNAi), also referred to as gene silencing, is based on using double-stranded RNA (dsRNA) molecules to turn genes off. When introduced into a cell, dsRNAs are processed by the cell into short fragments (generally about 21, 22, or 23 nucleotides in length) known as small interfering RNAs (siRNAs) which the cell uses in a sequence-specific manner to recognize and destroy complementary RNAs (Thompson, Drug Discovery Today, 7 (17): 912-917 (2002)). Accordingly, an aspect of the present invention specifically contemplates isolated nucleic acid molecules that are about 18-26 nucleotides in length, preferably 19-25 nucleotides in length, and more preferably 20, 21, 22, or 23 nucleotides in length, and the use of these nucleic acid molecules for RNAi. Because RNAi molecules, including siRNAs, act in a sequence-specific manner, the SNPs of the present invention can be used to design RNAi reagents that recognize and destroy nucleic acid molecules having specific SNP alleles/nucleotides (such as deleterious alleles that lead to the production of defective proteins), while not affecting nucleic acid molecules having alternative SNP alleles (such as alleles that encode proteins having normal function). As with antisense reagents, RNAi reagents may be directly useful as therapeutic agents (e.g., for turning off defective, disease-causing genes), and are also useful for characterizing and validating gene function (e.g., in gene knock-out or knock-down experiments).

The following references provide a further review of RNAi: Reynolds et al., "Rational siRNA design for RNA interference", Nat Biotechnol. 2004 March; 22(3):326-30. Epub 2004 Feb. 1; Chi et al., "Genomewide view of gene silencing by small interfering RNAs", PNAS 100(11):6343-6346, 2003; Vickers et al., "Efficient Reduction of Target RNAs by Small Interfering RNA and RNase H-dependent Antisense Agents", J. Biol. Chem. 278: 7108-7118, 2003; Agami, "RNAi and related mechanisms and their potential use for therapy", Curr Opin Chem Biol. 2002 December; 6(6):829-34; Lavery et al., "Antisense and RNAi: powerful tools in drug target discovery and validation", Curr Opin Drug Discov Devel. 2003 July; 6(4):561-9; Shi, "Mammalian RNAi for the masses", Trends Genet 2003 January; 19(1):9-12), Shuey et al., "RNAi: gene-silencing in therapeutic intervention", Drug Discovery Today 2002 October; 7(20): 1040-1046; McManus et al., Nat Rev Genet 2002 October; 3(10):737-47; Xia et al., Nat Biotechnol 2002 October; 20(10):1006-10; Plasterk et al., Curr Opin Genet Dev 2000 October; 10(5):562-7; Bosher et al., Nat Cell Biol 2000 February; 2(2):E31-6; and Hunter, Curr Biol 1999 Jun. 17; 9(12):R440-2).

A subject suffering from a pathological condition, such as drug overdose or underdose symptoms or propensity, ascribed to a SNP may be treated so as to correct the genetic defect (see Kren et al., Proc. Natl. Acad. Sci. USA 96:10349-10354 (1999)). Such a subject can be identified by any method that can detect the polymorphism in a biological sample drawn from the subject. Such a genetic defect may be permanently corrected by administering to such a subject a nucleic acid fragment incorporating a repair sequence that supplies the normal/wild-type nucleotide at the position of the SNP. This site-specific repair sequence can encompass an RNA/DNA oligonucleotide that operates to promote endogenous repair of a subject's genomic DNA. The site-specific repair sequence is administered in an appropriate vehicle, such as a complex with polyethylenimine, encapsulated in anionic liposomes, a viral vector such as an adenovirus, or other pharmaceutical composition that promotes intracellular uptake of the administered nucleic acid. A genetic defect leading to an inborn pathology may then be overcome, as the chimeric oligonucleotides induce incorporation of the normal sequence into the subject's genome. Upon incorporation, the normal gene product is expressed, and the replacement is propagated, thereby engendering a permanent repair and therapeutic enhancement of the clinical condition of the subject.

In cases in which a cSNP results in a variant protein that is ascribed to be the cause of, or a contributing factor to, a pathological condition, a method of treating such a condition can include administering to a subject experiencing the pathology the wild-type/normal cognate of the variant protein. Once administered in an effective dosing regimen, the wild-type cognate provides complementation or remediation of the pathological condition.

The invention further provides a method for identifying a compound or agent that can be used to treat drug overdose or underdose symptoms or propensity. The SNPs disclosed herein are useful as targets for the identification and/or development of therapeutic agents. A method for identifying a therapeutic agent or compound typically includes assaying the ability of the agent or compound to modulate the activity and/or expression of a SNP-containing nucleic acid or the encoded product and thus identifying an agent or a compound that can be used to treat a disorder characterized by undesired activity or expression of the SNP-containing nucleic acid or the encoded product. The assays can be performed in cell-based and cell-free systems. Cell-based assays can include cells naturally expressing the nucleic acid molecules of interest or recombinant cells genetically engineered to express certain nucleic acid molecules.

Variant gene expression in humans with drug overdose or underdose symptoms or propensity patient can include, for example, either expression of a SNP-containing nucleic acid sequence (for instance, a gene that contains a SNP can be transcribed into an mRNA transcript molecule containing the SNP, which can in turn be translated into a variant protein) or altered expression of a normal/wild-type nucleic acid sequence due to one or more SNPs (for instance, a regulatory/control region can contain a SNP that affects the level or pattern of expression of a normal transcript).

Assays for variant gene expression can involve direct assays of nucleic acid levels (e.g., mRNA levels), expressed protein levels, or of collateral compounds involved in a signal pathway. Further, the expression of genes that are up- or down-regulated in response to the signal pathway can also be assayed. In this embodiment, the regulatory regions of these genes can be operably linked to a reporter gene such as luciferase.

Modulators of variant gene expression can be identified in a method wherein, for example, a cell is contacted with a candidate compound/agent and the expression of mRNA determined. The level of expression of mRNA in the presence of the candidate compound is compared to the level of expression of mRNA in the absence of the candidate compound. The candidate compound can then be identified as a modulator of variant gene expression based on this comparison and be used to treat a disorder such as drug overdose or underdose symptoms or propensity that is characterized by variant gene expression (e.g., either expression of a SNP-containing nucleic acid or altered expression of a normal/wild-type nucleic acid molecule due to one or more SNPs that affect expression of the nucleic acid molecule) due to one or more SNPs of the present invention. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the SNP or associated nucleic acid domain (e.g., catalytic domain, ligand/substrate-binding domain, regulatory/control region, etc.) or gene, or the encoded mRNA transcript, as a target, using a compound identified through drug screening as a gene modulator to modulate variant nucleic acid expression. Modulation can include either up-regulation (i.e., activation or agonization) or down-regulation (i.e., suppression or antagonization) of nucleic acid expression.

Expression of mRNA transcripts and encoded proteins, either wild type or variant, may be altered in individuals with a particular SNP allele in a regulatory/control element, such as a promoter or transcription factor binding domain, that regulates expression. In this situation, methods of treatment and compounds can be identified, as discussed herein, that regulate or overcome the variant regulatory/control element, thereby generating normal, or healthy, expression levels of either the wild type or variant protein.

The SNP-containing nucleic acid molecules of the present invention are also useful for monitoring the effectiveness of modulating compounds on the expression or activity of a variant gene, or encoded product, in clinical trials or in a treatment regimen. Thus, the gene expression pattern can serve as an indicator for the continuing effectiveness of treatment with the compound, particularly with compounds to which a patient can develop resistance, as well as an indicator for toxicities. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

In another aspect of the present invention, there is provided a pharmaceutical pack comprising a therapeutic agent (e.g., a small molecule drug, antibody, peptide, antisense or RNAi nucleic acid molecule, etc.) and a set of instructions for administration of the therapeutic agent to humans diagnostically tested for one or more SNPs or SNP haplotypes provided by the present invention.

The SNPs/haplotypes of the present invention are also useful for improving many different aspects of the drug development process. For instance, an aspect of the present invention includes selecting individuals for clinical trials based on their SNP genotype. For example, individuals with SNP genotypes that indicate that they are likely to positively respond to a drug can be included in the trials, whereas those individuals whose SNP genotypes indicate that they are less likely to or would not respond to the drug, or who are at risk for suffering toxic effects or other adverse reactions, can be excluded from the clinical trials. This not only can improve the safety of clinical trials, but also can enhance the chances that the trial will demonstrate statistically significant efficacy. Furthermore, the SNPs of the present invention may explain why certain previously developed drugs performed poorly in clinical trials and may help identify a subset of the population that would benefit from a drug that had previously performed poorly in clinical trials, thereby "rescuing" previously developed drugs, and enabling the drug to be made available to a particular drug overdose or underdose symptoms patient population that can benefit from it.

SNPs have many important uses in drug discovery, screening, and development. A high probability exists that, for any gene/protein selected as a potential drug target, variants of that gene/protein will exist in a patient population. Thus, determining the impact of gene/protein variants on the selection and delivery of a therapeutic agent should be an integral aspect of the drug discovery and development process. (Jazwinska, A Trends Guide to Genetic Variation and Genomic Medicine, 2002 March; S30-S36).

Knowledge of variants (e.g., SNPs and any corresponding amino acid polymorphisms) of a particular therapeutic target (e.g., a gene, mRNA transcript, or protein) enables parallel screening of the variants in order to identify therapeutic candidates (e.g., small molecule compounds, antibodies, antisense or RNAi nucleic acid compounds, etc.) that demonstrate efficacy across variants (Rothberg, Nat Biotechnol 2001 March; 19(3):209-11). Such therapeutic candidates would be expected to show equal efficacy across a larger segment of the patient population, thereby leading to a larger potential market for the therapeutic candidate.

Furthermore, identifying variants of a potential therapeutic target enables the most common form of the target to be used for selection of therapeutic candidates, thereby helping to ensure that the experimental activity that is observed for the selected candidates reflects the real activity expected in the largest proportion of a patient population (Jazwinska, A Trends Guide to Genetic Variation and Genomic Medicine, 2002 March; S30-S36).

Additionally, screening therapeutic candidates against all known variants of a target can enable the early identification of potential toxicities and adverse reactions relating to particular variants. For example, variability in drug absorption, distribution, metabolism and excretion (ADME) caused by, for example, SNPs in therapeutic targets or drug metabolizing genes, can be identified, and this information can be utilized during the drug development process to minimize variability in drug disposition and develop therapeutic agents that are safer across a wider range of a patient population. The SNPs of the present invention, including the variant proteins and encoding polymorphic nucleic acid molecules provided herein, are useful in conjunction with a variety of toxicology methods established in the art, such as those set forth in Current Protocols in Toxicology, John Wiley & Sons, Inc., N.Y.

Furthermore, therapeutic agents that target any art-known proteins (or nucleic acid molecules, either RNA or DNA) may cross-react with the variant proteins (or polymorphic nucleic acid molecules) disclosed herein, thereby significantly affecting the pharmacokinetic properties of the drug. Consequently, the protein variants and the SNP-containing nucleic acid molecules disclosed in Tables 1-2 are useful in developing, screening, and evaluating therapeutic agents that target corresponding art-known protein forms (or nucleic acid molecules). Additionally, as discussed above, knowledge of all polymorphic forms of a particular drug target enables the design of therapeutic agents that are effective against most or all such polymorphic forms of the drug target.

DNA can be isolated from biological samples such as blood, bone, hair, saliva, or semen, and compared with the DNA from a reference source at particular SNP positions. Multiple SNP markers can be assayed simultaneously in order to increase the power of discrimination and the statistical significance of a matching genotype. For example, oligonucleotide arrays can be used to genotype a large number of SNPs simultaneously. The SNPs provided by the present invention can be assayed in combination with other polymorphic genetic markers, such as other SNPs known in the art or STRs, in order to identify an individual or to associate an individual with a particular biological sample.

Computer-Related Embodiments

The SNPs provided in the present invention may be "provided" in a variety of mediums to facilitate use thereof. As used in this section, "provided" refers to a manufacture, other than an isolated nucleic acid molecule, that contains SNP information of the present invention. Such a manufacture provides the SNP information in a form that allows a skilled artisan to examine the manufacture using means not directly applicable to examining the SNPs or a subset thereof as they exist in nature or in purified form. The SNP information that may be provided in such a form includes any of the SNP information provided by the present invention such as, for example, polymorphic nucleic acid and/or amino acid sequence information herein; information about observed SNP alleles, alternative codons, populations, allele frequencies, SNP types, and/or affected proteins; or any other information provided.

In one application of this embodiment, the SNPs of the present invention can be recorded on a computer readable medium. As used herein, "computer readable medium" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate manufactures comprising the SNP information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide/amino acid sequence information of the present invention on computer readable medium. For example, the sequence information can be represented in a word processing text file, formatted in commercially-available software such as WordPerfect and Microsoft Word, represented in the form of an ASCII file, or stored in a database application, such as OB2, Sybase, Oracle, or the like. A skilled artisan can readily adapt any number of data processor structuring formats (e.g., text file or database) in order to obtain computer readable medium having recorded thereon the SNP information of the present invention.

By providing the SNPs of the present invention in computer readable form, a skilled artisan can routinely access the SNP information for a variety of purposes. Computer software is publicly available which allows a skilled artisan to access sequence information provided in a computer readable medium. Examples of publicly available computer software include BLAST (Altschul et al., J. Mol. Biol. 215:403-410 (1990)) and BLAZE (Brutlag et al., Comp. Chem. 17:203-207 (1993)) search algorithms.

The present invention further provides systems, particularly computer-based systems, which contain the SNP information described herein. Such systems may be designed to store and/or analyze information on, for example, a large number of SNP positions, or information on SNP genotypes from a large number of individuals. The SNP information of the present invention represents a valuable information source. The SNP information of the present invention stored/analyzed in a computer-based system may be used for such computer-intensive applications as determining or analyzing SNP allele frequencies in a population, mapping disease genes, genotype-phenotype association studies, grouping SNPs into haplotypes, correlating SNP haplotypes with response to particular drugs, or for various other bioinformatic, pharmacogenomic, drug development, or human identification/forensic applications.

As used herein, "a computer-based system" refers to the hardware means, software means, and data storage means used to analyze the SNP information of the present invention. The minimum hardware means of the computer-based systems of the present invention typically comprises a central processing unit (CPU), input means, output means, and data storage means. A skilled artisan can readily appreciate that any one of the currently available computer-based systems are suitable for use in the present invention. Such a system can be changed into a system of the present invention by utilizing the SNP information provided on the CD-R, or a subset thereof, without any experimentation.

As stated above, the computer-based systems of the present invention comprise a data storage means having stored therein SNPs of the present invention and the necessary hardware means and software means for supporting and implementing a search means. As used herein, "data storage means" refers to memory which can store SNP information of the present invention, or a memory access means which can access manufactures having recorded thereon the SNP information of the present invention.

As used herein, "search means" refers to one or more programs or algorithms that are implemented on the computer-based system to identify or analyze SNPs in a target sequence based on the SNP information stored within the data storage means. Search means can be used to determine which nucleotide is present at a particular SNP position in the target sequence. As used herein, a "target sequence" can be any DNA sequence containing the SNP position(s) to be searched or queried.

As used herein, "a target structural motif," or "target motif," refers to any rationally selected sequence or combination of sequences containing a SNP position in which the sequence(s) is chosen based on a three-dimensional configuration that is formed upon the folding of the target motif. There are a variety of target motifs known in the art. Protein target motifs include, but are not limited to, enzymatic active sites and signal sequences. Nucleic acid target motifs include, but are not limited to, promoter sequences, hairpin structures, and inducible expression elements (protein binding sequences).

A variety of structural formats for the input and output means can be used to input and output the information in the computer-based systems of the present invention. An exemplary format for an output means is a display that depicts the presence or absence of specified nucleotides (alleles) at particular SNP positions of interest. Such presentation can provide a rapid, binary scoring system for many SNPs simultaneously.

One exemplary embodiment of a computer-based system comprising SNP information of the present invention includes a processor connected to a bus. Also connected to the bus are a main memory (preferably implemented as random access memory, RAM) and a variety of secondary storage devices, such as a hard drive and a removable medium storage device. The removable medium storage device may represent, for example, a floppy disk drive, a CD-ROM drive, a magnetic tape drive, etc. A removable storage medium (such as a floppy disk, a compact disk, a magnetic tape, etc.) containing control logic and/or data recorded therein may be inserted into the removable medium storage device. The computer system includes appropriate software for reading the control logic and/or the data from the removable storage medium once inserted in the removable medium storage device.

The SNP information of the present invention may be stored in a well-known manner in the main memory, any of the secondary storage devices, and/or a removable storage medium. Software for accessing and processing the SNP information (such as SNP scoring tools, search tools, comparing tools, etc.) preferably resides in main memory during execution.

Also provided is a research system in which embodiments may be implemented. The research system includes a study data analysis system. The study data analysis system may be used, for example, to store, recall, access, implement, or otherwise use datasets or other information obtained from study data.

The study data analysis system may be used, for example, to identify agent(s) associated with one or more treatment targets which are associated with a specific subpopulation(s) of individuals for whom the incidence of one or more adverse events is acceptable at a defined level. The study data analysis system may identify such agent(s) by, for example, storing, analyzing and/or providing datasets or other information obtained from study data as to the safety and optionally, the effectiveness, of the agent(s).

A drug overdose or underdose event, also known as an adverse effect, side effect, or complication, is typically a consequence of agent administration other than the intended consequence of agent administration. In certain embodiments, an adverse event as used herein may have a neutral consequence to an individual, or an adverse event may actually have beneficial effects on an individual though such beneficial effects may be unintended consequences of administration. Examples of adverse events are, without limitation, swelling, pain, nausea, diarrhea, change in blood pressure or other physiological measure, headache, heart attack, allergy, death, and unintended changes in gene expression, protein expression or biochemical activity.

An agent, as used herein, can be, for example, a medical or non-medical intervention, including, for example, administration of prescription or non-prescription medications, small molecule drugs or biologics, nutraceuticals, or dietary supplements. An agent may also be, for example, alcohol or an illicit substance. A treatment target, as used herein, can be, for example, a medical condition, treatment goal or disorder meriting clinical, nutraceutical or alternative medical intervention. Treatment targets may also be voluntary procedures, for example, cosmetic procedures. Treatment, as used herein, can refer to treating and/or prevention. A treatment target is search of an agent is a treatment target of interest (e.g., a medical condition) for which the incidence and/or severity of an adverse event(s) under a standard of care is high and/or unacceptable.

As a further example, the study data analysis system can provide information about which agent(s) are candidates for further testing and development according to defined levels of tolerance for one or more adverse events and/or defined efficacy levels. On the basis of study data analysis, for example, for a given treatment target in search of an agent, an agent may be identified through the use of a query parameter that functions to identify subsets of data that correspond to a certain level of adverse event that is different from that of a population for which the adverse event level is unacceptable. Thus, identified agents exhibit acceptable levels of adverse events in a subset of the data, and optionally are effective in treating the condition at a defined level.

The analysis system is used by a clinical researcher. The clinical researcher, for example, may use the study data analysis system to enter, store, request, or access study data relating to a treatment target, medical condition, or prevention target, such as, for example, the various examples provided herein. The clinical researcher may generally represent, for example, a person involved in health care or the health care industry, including, for example, a pharmaceutical company researcher or clinician, a biotechnology company researcher or clinician, a doctor, or a biomedical researcher. The clinical researcher also may represent someone who is involved in health care in the sense of developing, managing, or implementing the study data analysis system, e.g., a software developer with clinical knowledge (or access to clinical knowledge), a database manager, or an information technologies specialist. Even more generally, some or all of various functions or aspects described herein with respect to the clinical researcher may be performed automatically, e.g., by an appropriately-designed and implemented computing device, or by software agents or other automated techniques.

Study data is typically data relating to conditions of agent testing, agent dosing and administration schedule, delivery system(s), efficacy, mechanism(s) of action, adverse events, pharmacokinetics, pharmacodynamics, statistical parameters and outcomes, and/or other experimental conditions or results. Study data also may represent or include diagnostic testing, for example, to determine the safety and/or efficacy of a particular agent such as a medication, medical device or surgical treatment. Study data may originate from, for example, an experiment and may be found in one or more different sources, including, for example, published journal articles, clinical trial reports, data reported on internet site(s), data submitted to the Food and Drug Administration or other regulatory agency, data included in pharmacogenomic database(s), data included in genetic database(s), or data found in other relevant database(s) that contain data relating to the conditions of use, effect, mechanism of action or other properties of an agent relevant to a treatment target. Study data may also originate from a mathematical and/or computer simulation(s) of one or more properties of an agent, for example, data from an in vitro/in vivo correlation analysis. Study data, for example, could result from preclinical testing or clinical testing, and may include data from in vitro testing, in situ testing, in vivo testing in animals or clinical testing in human subjects or patients. A formal clinical trial is one example of a study that results in study data.

Study data may include raw data, for example, agent name, agent concentration, dosing, dosing frequency, agent concentration in the blood following administration at various times, minimum and maximum blood concentrations ($C_{min}$ and $C_{max}$, respectively), the times at which $C_{min}$ and $C_{max}$ occur ($T_{min}$ and $T_{max}$, respectively), measured effect of the agent(s) on blood protein, lipid or cell levels, and/or reported adverse events experienced by study participants.

Study data may also include study participant data or other information such as, for example, age, weight, gender, race, ethnicity, dietary factors, medical history, concomitant medications, and other demographic characteristics. Study data may also include molecular information about study participants such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Study data may include data points that are, for example, ordinals, nominals, binaries, genetic, and/or continuous.

As a further example, the study data analysis system (including agent identification logic and subset identification logic) may accept an input associated with a query parameter to determine within study data one or more subsets of study data corresponding to population(s) having a defined level of tolerance for one or more adverse events relative to a population for which the adverse event profile is unacceptable with respect to the defined limit and, optionally, a defined efficacy level. The query parameter, for example, may specify a level of adverse event that serves to limit the study data to a specific subset of study data containing, for example, a desired incidence of a certain adverse event. Study data may report adverse event levels and/or efficacy levels; it is understood that such reported data may or may not precisely match actual adverse event levels and/or efficacy levels.

The study data analysis system also may correlate subset adverse event data with subpopulation identifier data to identify one or more clinically relevant patient populations. For example, an agent may be identified using the study data analysis system which exhibits tolerable adverse events in a subset of study data that is characterized by a particular molecular marker. The study data analysis system may then be used to further search, for example, one or more population databases to find subpopulation identifier data that correlate the molecular marker with one or more clinically relevant patient populations. Such population databases may include, for example, those that contain molecular information about individuals or populations such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Ongoing, prospective and completed clinical trials for various agents may be found in databases such as government or private clinical trial websites, which lists specific details for clinical trials, including primary and secondary outcomes, enrollment size, inclusion and exclusion criteria, and other parameters. In addition, clinical trial results are generally available in journal publications that are known to, and accessible by, persons of ordinary skill in the art.

The study data analysis system (including agent identification logic and/or subset identification logic) may apply appropriate statistical methods to study data, which may provide, for example, an average value(s) for a set of data, a confidence level(s) for a confidence interval(s), p-value(s), or other measures of statistical significance for multiple data points in one or more data sets, such as observed or simulated study data. Such statistical methods may comprise the query parameter of the subject matter. For example, the study data analysis system may include subset identification logic that is capable of applying an input associated with a query parameter to study data as a means of selecting relevant and/or statistically significant data.

Study data relating to safety and efficacy of an agent in terms of treating, for example, a medical condition, often is associated with a statistical measure of significance in terms of, for example, a clinical endpoint of an experimental trial. For example, an agent administered to patients with a medical condition, according to a defined dosing schedule, may relieve one or more symptoms of the medical condition to an extent that is statistically significant when compared to the effect of a placebo. Further, administration of the agent may result in a statistically significantly higher incidence of an adverse event than is observed following administration of a placebo.

In this regard, it should be understood that the study data analysis system can, for a given treatment target in search of an agent, (1) identify agents that are associated with an unacceptable level of adverse events in the context of a user-supplied input query parameter; (2) apply such a query parameter to identify a subset of data that is associated with a defined level of adverse events relative to the population for which the adverse event level is unacceptable; and (3) present the agent based on the subset of study data and the query parameter.

For example, many databases may be searched singly or in combination to identify one or more agents that exhibit a particular level of adverse events in the context of treating a given condition. Similarly, many databases exist that may be searched singly or in combination to identify one or more subsets of data corresponding to a defined tolerance for at least one adverse event upon administration of the one or more agents. Similarly, many databases exist that may be searched singly or in combination to identify one or more subpopulations having a defined level of efficacy upon administration of the one or more agent.

Databases that contain study data relating to, for example, the genetic make-up of a population, agent efficacy, and/or agent adverse events include, for example, those found on the internet at the Entrez websites of the National Center for Biotechnology Information (NCBI). NCBI databases are internally cross-referenced and include, for example, medical literature databases such as PubMed and Online Mendelian Inheritance in Man; nucleotide databases such as GenBank; protein databases such as SwissProt; genome databases such as Refseq; and expression databases such as Gene Expression Omnibus (GEO). Also useful are publication databases such as Medline and Embase.

Another useful resource includes the Pharmacogenomics Knowledgebase, PharmGKB, sponsored by the U.S National Institute of Health and hosted by Stanford University. Yet another useful resource is The Human Cytochrome P450 (CYP) Allele Nomenclature Database.

Other databases include, for example, IMS Health databases of prescribing information and patient reporting information such as that contained in the National Disease and Therapeutic Index (NDTI) database, which provides a large survey of detailed information about the patterns and treatment of disease from the viewpoint of office-based physicians in the continental U.S. Also of use is the U.S. Food and Drug Administration's (FDA's) Adverse Event Reporting System (AERS) database. This database contains adverse drug reaction reports from manufacturers as required by FDA regulation. In addition, health care professionals and consumers send reports voluntarily through the MedWatch program. These reports become part of a database. The structure of this database is in compliance with the international safety reporting guidance issued by the International Conference on Harmonization. The FDA codes all reported adverse events using a standardized international terminology called MedDRA (the Medical Dictionary for Regulatory Activities). Among AERS system features are the on-screen review of reports, searching tools, and various output reports. Another adverse drug events database is DIOGENES®, a database consisting of two sub-files: Adverse Drug Reactions (ADR) and Adverse Event Reporting System (AERS). ADR records contain data regarding a single patient's experience with a drug or combination of drugs as reported to the FDA. Since 1969, the FDA has legally-mandated adverse drug reaction reports from pharmaceutical manufacturers and maintained them in their ADR system. In November 1997, the ADR database was replaced by the AERS. Other adverse event reporting databases include, for example, the Vaccine Adverse Event Reporting System (VAERS) and the Manufacturer and User Facility Device Experience Database (MAUDE).

What is claimed is:

1. A method of administering a dose of a medication to a human in need thereof, comprising: determining the human's metabolizer status genotype for a panel of cytochrome P450 CYP3A alleles according to the following:
   i.) extensive metabolizer status if CYP3A4 genotype at rs35599367 is CC and CYP3A5 genotype at rs776746 is AA and CYP3A5 genotype at rs41303343 is a T insertion;
   ii.) intermediate metabolizer status if CYP3A4 genotype at rs35599367 is CT and CYP3A5 genotype at rs776746 is AG and CYP3A5 genotype at rs41303343 is a T deletion;
   ii.) poor metabolizer status if CYP3A4 genotype at rs35599367 is TT and CYP3A5 genotype at rs776746 is GG and CYP3A5 genotype at rs41303343 is (del T)(del T); administering a dose of medication according to metabolizer status, wherein:
   if the human is determined to be an extensive metabolizer, the dose is high,
   if the human is determined to be an intermediate metabolizer, the dose is standard, or if the human is determined to be a poor metabolizer, the dose is low;
wherein a high dose is 1.5 to 2.5 times a standard dose, and wherein a low dose is 0.25 to 0.75 of a standard dose.

2. A method of claim 1, which further comprises communicating the data or risk to at least one human.

3. A method of claim 1, wherein the at least one genotyping assay is selected from the group consisting of: polymerase chain reaction (PCR), DNA fragment analysis, allele specific oligonucleotide (ASO) probes, DNA sequencing, and nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA).

4. A method of claim 1, which further comprises measuring the level of at least one additional liver cytochrome marker in the test sample.

5. A method of claim 1, wherein said assay is performed using sequencing, 5' nuclease digestion, molecular beacon assay, oligonucleotide ligation assay, size analysis, single-stranded conformation polymorphism, or denaturing gradient gel electrophoresis (DGGE).

6. A method of claim 1, wherein said nucleic acid is a nucleic acid extract from a biological sample from said human.

7. A method of claim 6, in which said biological sample is blood, saliva, buccal cells, tissue, plasma, serum, urine, or feces.

8. A method of claim 1, further comprising providing a report of the identity of the SNP profile.

9. A method of claim 1 further comprising providing a report of said human's increased risk for developing drug overdose or underdose symptoms.

* * * * *